(12) United States Patent
Vij et al.

(10) Patent No.: US 8,273,700 B2
(45) Date of Patent: Sep. 25, 2012

(54) METHODS AND COMPOSITIONS FOR TREATMENT OF CYSTIC FIBROSIS

(75) Inventors: Neeraj Vij, Baltimore, MD (US); Pamela L. Zeitlin, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 531 days.

(21) Appl. No.: 11/992,799

(22) PCT Filed: Sep. 29, 2006

(86) PCT No.: PCT/US2006/038031
§ 371 (c)(1),
(2), (4) Date: May 3, 2010

(87) PCT Pub. No.: WO2007/041282
PCT Pub. Date: Apr. 12, 2007

(65) Prior Publication Data
US 2010/0222408 A1    Sep. 2, 2010

Related U.S. Application Data

(60) Provisional application No. 60/722,049, filed on Sep. 29, 2005.

(51) Int. Cl.
*A01N 61/00* (2006.01)
*A01N 37/18* (2006.01)
*A01N 43/04* (2006.01)

(52) U.S. Cl. .................. 514/1; 514/2; 514/44

(58) Field of Classification Search ............ 435/6, 91.1, 435/91.31, 375; 514/1, 2, 44; 536/23.1, 536/24.5
See application file for complete search history.

(56) References Cited

OTHER PUBLICATIONS

Dai et al., J. Biol. Chem., vol. 273, No. 6, pp. 3562-3573 (1998).*
Griesenbach et al, Gene Therapy, vol. 7, pp. 306-313 (2000).*
Brouillard et al, J. Biol. Chem., vol. 276, No. 12, pp. 9486-9491 (2001).*
Tabry et al., Eru. J. Physiol., vol. 443, Suppl. 1, S40-S44 (2001).*
Asai et al., Jpn. J. Cancer Res., vol. 93, pp. 296-304 (2002).*
Nan et al., Expl. & Molec. Pathol., vol. 78, pp. 1-9 (2005).*
Nan L et al. "RNA interference of VCP/p97 increases Mallory body formation." Exp Mol Pathol. Feb. 2005;78(1):1-9.
Wójcik C et al. "RNA interference of valosin-containing protein (VCP/p97) reveals multiple cellular roles linked to ubiquitin/proteasome-dependent proteolysis." J Cell Sci. Jan. 15, 2004;1 17(Pt 2):281-92.
Wójcik C et al. "Modulation of gene expression by RNAi." Methods Mol Med. 2005;108:381-93.
Zhong X et al. "AAA ATPase p97/valosin-containing protein interacts with gp78, a ubiquitin ligase for endoplasmic reticulum-associated degradation." J Biol Chem. Oct. 29, 2004;279(44):45676-84.
International Search Report for PCT/US06/38031 filed Sep. 29, 2006, published as WO 2007/041282 A3 on Apr. 12, 2007 issued on May 23, 2007, mailed Aug. 6, 2007.

* cited by examiner

*Primary Examiner* — Jane Zara
(74) *Attorney, Agent, or Firm* — Edwards Wildman Palmer LLP; Peter F. Corless; Melissa Hunter-Ensor, Esq.

(57) ABSTRACT

The present invention relates to compounds and methods of inhibiting p97/valosin-containing protein and compounds and methods of inhibiting gp78, the compounds and methods being useful for the treatment of a disorder comprising a IκB/NFκB mediated chronic inflammatory response component, for example cystic fibrosis.

1 Claim, 14 Drawing Sheets

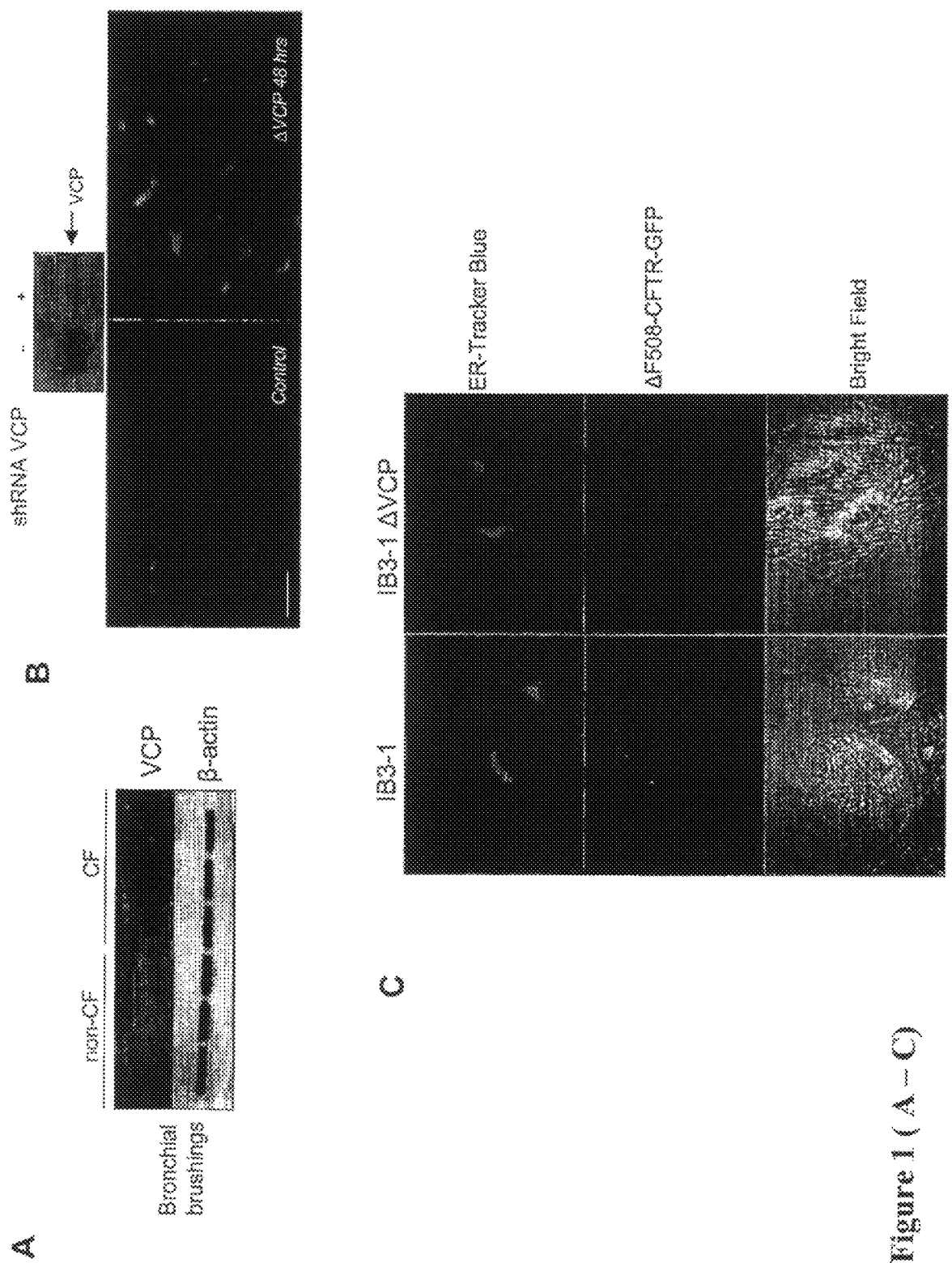
Figure 1 (A – C)

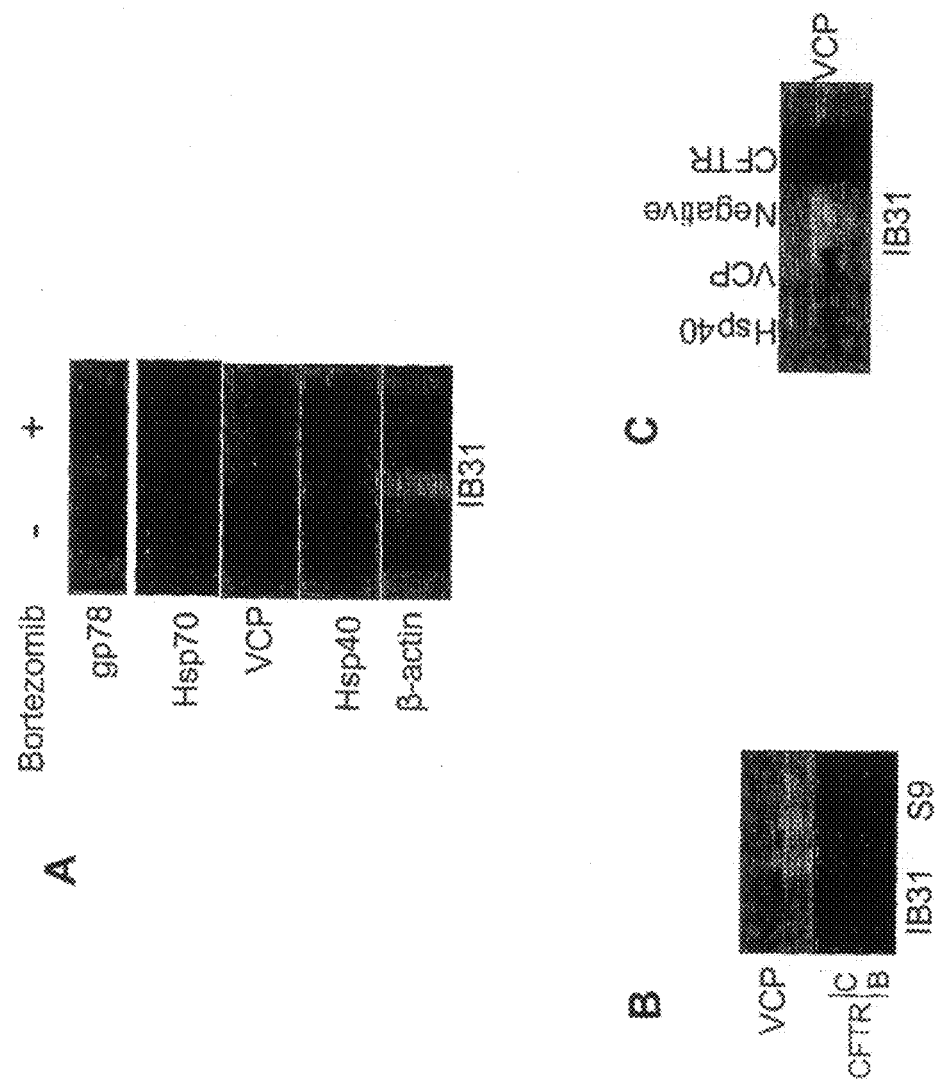
Figure 3 (A – C)

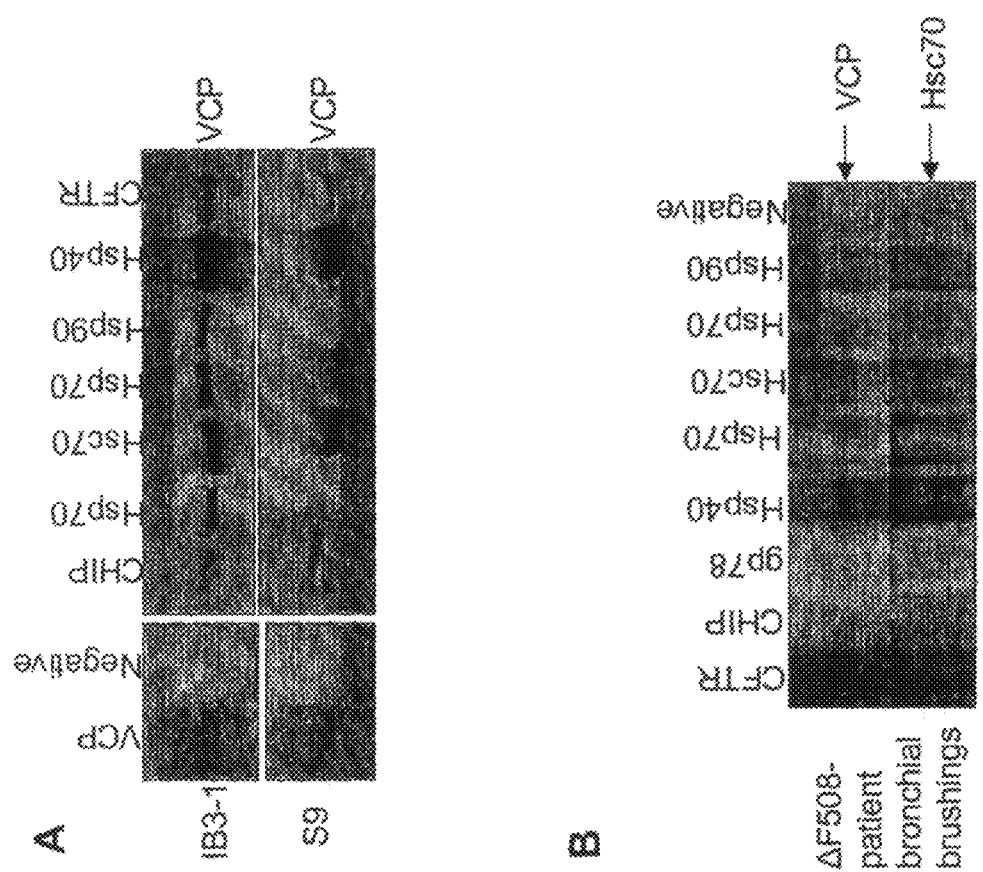
Figure 4 (A & B)

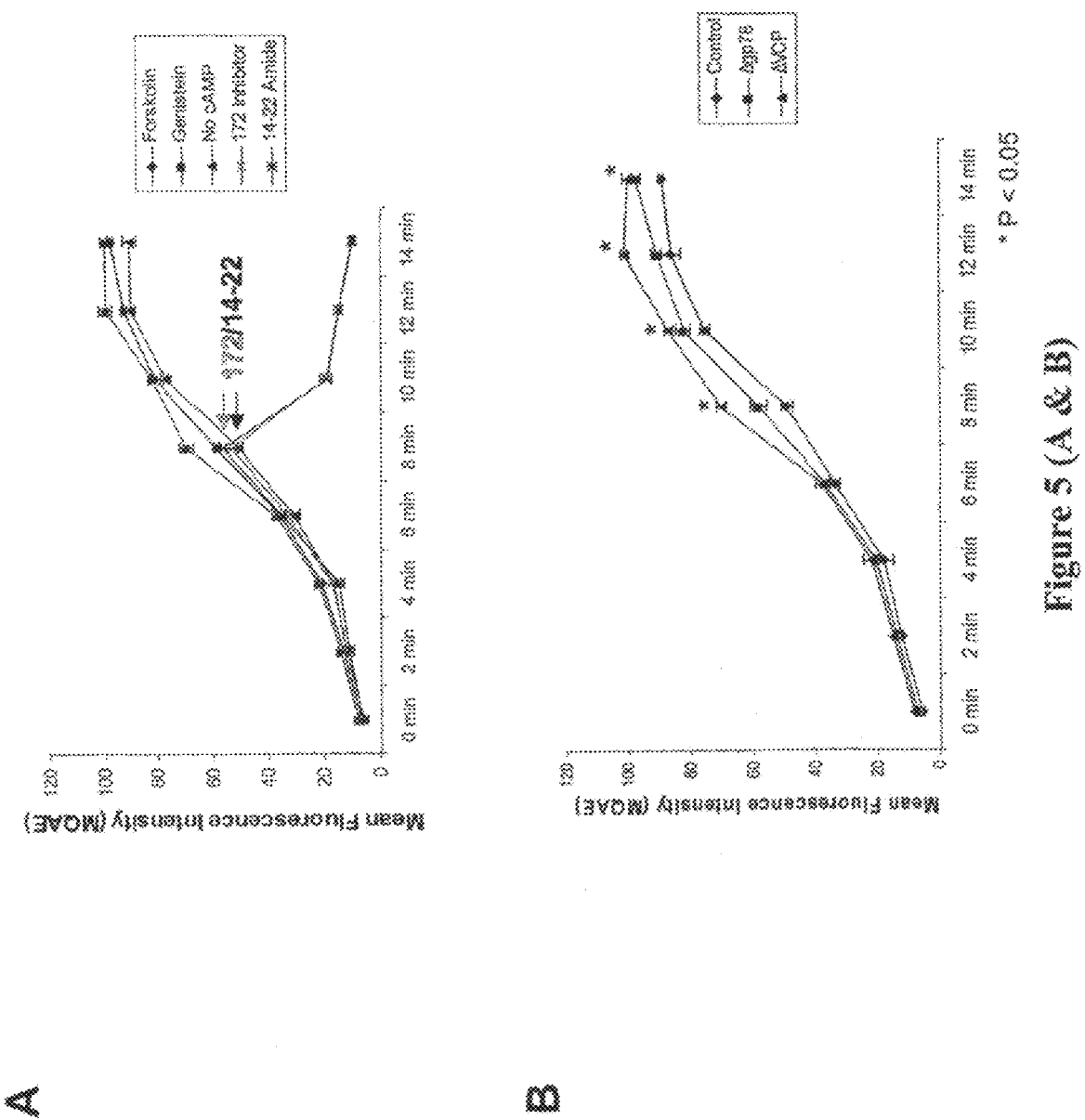
Figure 5 (A & B)

SEQ ID NO: 1  CCCGCAAGAAGATGGATCTCAT

SEQ ID NO: 2  ATGAGATCCATCTCTTGCGGA

Figure 8

SEQUENCE LISTING

<160> NUMBER OF SEQ ID NOS: 5

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cccgcaagaa gatggatctc at                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atgagatcca tcttcttgcg ga                                              22

<210> SEQ ID NO 3
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgctgttgac agtgagcgcc cgcaagaaga tggatctcat tagtgaagcc acagatgtaa     60
tgagatccat cttcttgcgg atgcctactg cctcgga                              97

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cagaaggctc gagaaggtat attgctgttg acagtgagcg                           40

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctaaagtagc cccttgaatt ccgaggcagt aggca                                35

METHODS AND COMPOSITIONS FOR TREATMENT OF CYSTIC FIBROSIS

STATEMENT OF RIGHTS TO INVENTIONS MADE UNDER FEDERALLY SPONSORED RESEARCH

This invention was funded, at least in part, by NIH grants R01HL51811 and R01HL59410. Accordingly, the U.S. Government may have certain rights to this invention.

CROSS-REFERENCE TO RELATED APPLICATIONS/PATENTS & INCORPORATION BY REFERENCE

This application claims the benefit of U.S. Provisional Application No. 60/722,049, filed Sep. 29, 2005, the entire contents of which are expressly incorporated herein by reference. Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List before the paragraphs, or in the text itself; and, each of these documents or references ("herein-cited references"), as well as each document or reference cited in each of the herein-cited references (including any manufacturer's specifications, instructions, etc.), is hereby expressly incorporated herein by reference.

BACKGROUND OF THE INVENTION

1. Field of the Invention

The present invention relates to compounds and methods for treating a disorder and/or condition having a IκB/NFκB-mediated chronic inflammatory response (e.g. cystic fibrosis)

2. Background

The IκB/NFκB-mediated chronic inflammatory response is a known component of a variety of diseases and disorders, including, for example, cystic fibrosis, diabetes, Parkinson's Disease, Alzheimer's Disease and others. NFκB is a transcription factor which mediates extracellular signals responsible for induction of genes involved in pro-inflammatory responses (see U.S. Pat. No. 5,804,374), including the production of various cytokines such as interleukin-8 (IL-8). NFκB is anchored in the cytoplasm of most non-stimulated cells by a non-covalent interaction with one of several inhibitory proteins known as IκBs (see May & Ghosh, (1997) Semin. Cancer. Biol. 8, 63-73; May & Ghosh, (1998) Immunol. Today 19, 80-88; Ghosh et al., (1998) Annu. Rev. Immunol. 16, 225-260). Cellular stimuli associated with pro-inflammatory responses in turn activate NFκB through the phosphorylation of the IκBs. Phosphorylation targets IκBs for ubiquitination and degradation by the proteasome. The degradation and subsequent dissociation of IκBs from NFκB reveals the nuclear localization signal on NFκB, resulting in nuclear translocation of active NFκB, leading to up-regulation of genes responsive to NFκB, which include various cytokine such as IL8 associated with a variety of disorders (May & Ghosh, (1997) Semin. Cancer. Biol. 8, 63-73; May & Ghosh, (1998) Immunol. Today 19, 80-88; Ghosh et al., (1998) Annu. Rev. Immunol. 16, 225-260; Siebenlist et al., (1994) Annu. Rev. Cell Biol. 12, 405-455).

One important disease which involves in part an NFκB mediated pro-inflammatory response is cystic fibrosis. This disease is the most common lethal recessive genetic disease in the United States (Di Sant' Agrese et al., Am J. Med. (1979) 66:121-132). In the United States, the disease occurs once in every 1500 to 2000 Caucasian live births and once in every 17,000 Afro-American live births (Steinbert et al., Am. J. Human Genet. (1969) 12:416-424; ICramm et al., Am. J. Public Health (1962) 52:2041-2051; Merritt, et al., J. Lab. Clin. Med. (1962) 60:990-999; and Shultz et al., Am. J. Public Health (1966) 56:1461-1469). Despite current standard therapy, the median age of survival is only 26 years, wherein about 50% of individuals with cystic fibrosis die before reaching the age of 21 years.

The major cause of mortality and morbidity in patients with cystic fibrosis is progressive pulmonary disease, which is responsible for about 95% of the mortality (Stern et al., J. Pediatrics (1976) 89:406-411). In cystic fibrosis individuals, lung disease is not present at birth but typically develops later during childhood or adolescence (Sturgess et al., Am. J. Pathol. (1992); 106:303-311).

While great progress has been made, much still is unknown about the pathogenesis of cystic fibrosis. In the early stages of disease, inflammation of small airway leads to the formation of lesions. This early inflammation is generally thought to be linked to bacterial infection as cystic fibrosis patients have distinctive respiratory flora (Mearns et al., Arch. Dis. Child (1972) 47:902-907). In particular, *Staphylococcus aureus* is generally the dominant organism early in the course of cystic fibrosis disease, which is supplanted later in disease progression by *Pseudomonas aeruginosa*, and in particular mucoid strains of *P. aeruginosa* (Tococca et al., Am. J. Dis. Child (1963) 106:315-325).

As infections and inflammation become established in airways of the cystic fibrosis patient, hypertrophy and hyperplasia of the mucous-secreting apparatus develops, ciliated cells are replaced by goblet cells, and squamous metaplasia becomes pronounced. Beneath impacted mucous, denudation and ulceration of the mucosa may occur. Gradually, this destruction progresses up the respiratory tree to involve the larger airways. Structural damage to the bronchial wall occurs, and bronchiectasis develops. Bronchiectasis and mucopurulent plugging are present in most cystic fibrosis patients even at very early ages (Bedrossian et al, Human Pathol. (1976) 7:195-204.).

Several factors contribute to the progression of lung disease in cystic fibrosis patients. One of the most important factors, however, is the thick, viscous nature of airway mucous. Not only do thick secretions obstruct airways and contribute to reduced lung volumes and expiratory flows, but they also cause the inflammatory process to stand within the airways, thereby exposing the airway mucosa to a more abundant protease and oxidant rich environment than if the purulent respiratory secretions were easily expectorated. The enhanced viscoelastic properties of purulent secretions is due in part to the presence of highly polymerized, polyanionic deoxyribonucleic acid (DNA) from the nuclei of degenerating polymorphonuclear neutrophils (PMNs). Also, contributing to sputum tenacity is the presence of abundant cross-linked actin filaments from the cytosol of PMNs.

Upper airways of the nose and sinuses are also involved in cystic fibrosis. For example, most patients develop chronic sinusitis. Nasal polyps occur in 15-20% of patients and are common by the second decade of life. In addition, gastrointestinal problems are frequent in cystic fibrosis. Infants, in particular, may suffer meconium ileus. Further, exocrine pancreatic insufficiency, which produces symptoms of malabsorption, is present in the large majority of patients with cystic fibrosis. Males are almost uniformly infertile and fertility is decreased in females.

The protein product of the cystic fibrosis associated gene is called the cystic fibrosis transmembrane conductance regulator (CFTR) (Riordan, J. R. et al. (1989) Science 245:1066-1073). CFTR is a protein of approximately 1480 amino acids made up of two repeated elements, each comprising six transmembrane segments and a nucleotide binding domain. The two repeats are separated by a large, polar, so-called R-domain containing multiple potential phosphorylation sites. Based on its predicted domain structure, CFTR is a member of a class of related proteins which includes the multi-drug resistance (MDR) or P-glycoprotein, bovine adenyl cyclase, the yeast STE6 protein as well as several bacterial amino acid transport proteins (Riordan, J. R. et al. (1989) Science 245: 1066-1073; Hyde. S. C. et al. (1990) Nature 346:362-365). Proteins in this group, characteristically, are involved in pumping molecules into or out of cells.

CNTR has been postulated to regulate the outward flow of anions from epithelial cells in response to phosphorylation by cyclic AMP-dependent protein kinase or protein kinase C (Riordan, J. R. et al. (1989) Science 245:1066-1073; Frizzell, R. A. et al. (1986) Science 233:558-560; Welsh, M. J. and Liedtke, C. M. (1986) Nature 322:467; Li, M. et al. (1988) Nature 331:358-360; Hwang, T-C. et al. (1989) Science 244: 1351-1353).

Sequence analysis of the CFTR gene of cystic fibrosis chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). Population studies have indicated that the most common cystic fibrosis mutation is a deletion of the 3 nucleotides that encode phenylalanine at position 508 of the CFTR amino acid sequence (ΔF508-CFTR), which is associated with approximately 70% of cystic fibrosis cases. This mutation results in the failure of an epithelial cell chloride channel to respond to cAMP (Frizzell R. A. et al. (1986) Science 233:558-560; Welsh, M. J. (1986). Science 232:1648-1650; Li, M. et al. (1988) Nature 331:358-360; Quinton, P. M. (1989) Clin. Chem. 35:726-730). In airway cells, this leads to an imbalance in ion and fluid transport. It is widely believed that this causes abnormal mucus secretion, disrupted luminal hydration, heightened immune response and ultimately results in pulmonary infection and epithelial cell damage described above.

To date, the primary objectives of treatment for cystic fibrosis have been to control infection, promote mucus clearance, and improve nutrition (Boat, T. F. et al. in The Metabolic Basis of Inherited Diseases (Scriver, C. R. et al. eds., McGraw-Hill, New York (1989)). Intensive antibiotic use and a program of postural drainage with chest percussion are the mainstays of therapy. However, as the disease progresses, frequent, hospitalizations are required. Nutritional regimens include pancreatic enzymes and fat-soluble vitamins. Bronchodilators are used at times. Corticosteroids have been used to reduce inflammation, but they may produce significant adverse effects and their benefits are not certain. In extreme cases, lung transplantation is sometimes attempted (Marshall, S. et al. (1990) Chest 98:1488).

Currently known approaches for dealing with cystic fibrosis generally include both therapies and/or treatments that are targeted towards ameliorating the symptoms of cystic fibrosis, e.g. pulmonary mucus therapies, and treatments that target the underlying genetics and/or pathophysiology of the disease, e.g. underlying immune response and genetics of the disease. In one exemplary approach, pharmacological treatments aimed at correcting the abnormalities in electrolyte transport associated with cystic fibrosis are being pursued. In another approach, "protein replacement" seeks to deliver functional, recombinant CFTR to cystic fibrosis mutant cells to directly augment the missing CFTR activity. Protein replacement therapy for cystic fibrosis could include a preparation of highly purified recombinant CFTR formulated in an appropriate carrier suitable for delivery to the airways by instillation or aerosol. Such replacement therapeutics have met with many difficulties, however, not the least of which includes the difficulty in purification of and handling of CFTR. Still in a further approach, gene therapy has been explored by which DNA encoding CFTR is transferred to CFTR defective cells (e.g. of the respiratory tract). However, methods to introduce DNA into cells are generally inefficient, unpredictable, and pose many health risks.

Cystic fibrosis, like many other disorders, is in part an inflammatory disease. Inflammation is defined as the reaction of vascularized living tissue to injury. As such, inflammation is a fundamental, stereotyped complex of cytologic and chemical reactions of affected blood vessels and adjacent tissues in response to an injury or abnormal stimulation caused by a physical, chemical or biological agent Inflammation usually leads to the accumulation of fluid and blood cells at the site of injury, and is usually a healing process. However, inflammation sometimes causes harm, usually through a dysfunction of the normal progress of inflammation. Inflammatory diseases are those pertaining to, characterized by, causing, resulting from, or becoming affected by inflammation. Examples of inflammatory diseases or disorders or those having an inflammatory component, besides cystic fibrosis include, without limitation, asthma, lung inflammation, chronic granulomatous diseases such as tuberculosis, leprosy, sarcoidosis, and silicosis, nephritis, amyloidosis, rheumatoid arthritis, ankylosing spondylitis, chronic bronchitis, scleroderma, lupus, polymyositis, appendicitis, inflammatory bowel disease, ulcers, Sjorgen's syndrome, Reiter's syndrome, psoriasis, pelvic inflammatory disease, orbital inflammatory disease, thrombotic disease, and inappropriate allergic responses to environmental stimuli such as poison ivy, pollen, insect stings and certain foods, including atopic dermatitis and contact dermatitis, diabetes insipidus, Type II diabetes, Parkingson's Disease, Alzheimer's Disease, amyloidosis, surfactant protein C deficiency, ABCA3 deficiency, Huntington's Disease, adrenoleukodystrophy, amyotrophic lateral sclerosis, retinitis pigmentosa, polylutamine disease, mad cow disease, alpha one antitrypsin deficiency, short chain acyl CoA dehydrogenase deficiency, inclusion body myositis, and the aging process. The inflammation characteristic of many of the above inflammatory diseases (or those having an inflammatory component) can be linked to the aforementioned NFκB-mediated chronic inflammatory response pathway.

Although there has been notable progress in understanding the basis of inflammatory diseases, many of the therapies for controlling inflammatory diseases and disorders, and especially for treating cystic fibrosis, possess obstacles and disadvantages. Accordingly, therapies for treating cystic fibrosis and other diseases and disorders having a NFκB-mediated chronic inflammatory response component are needed.

Citation or identification of any document in this application is not an admission that such document is available as prior art to the present invention.

SUMMARY OF THE INVENTION

The present invention generally provides methods and compounds for treating a disorder and/or condition that involves the endoplasmic reticulum associated degradation (ERAD) pathway and/or the ubiquitin-proteasome system and/or which can be characterized as having a IκB/NFκB-mediated chronic inflammatory response (e.g. cystic fibrosis). The present invention especially relates to compositions and methods for selectively inhibiting cellular degradation of cystic fibrosis transmembrane regulator (CFTR) by the endoplasmic reticulum associated degradation (ERAD) pathway and/or ubiquitin-proteasome system, through the blocking of interactions between p97/valosin-containing protein and/or gp78 with CFTR. The present invention further relates to composition and methods for selectively inhibiting cellular degradation of IκB by the ubiquitin-proteasome system, and thus, maintaining and/or promoting the inhibition of the IκB/NFκB-mediated chronic inflammatory response, through blocking and/or minimizing interactions between p97/valosin-containing protein and IκB. The invention further relates to the selective inhibition of cellular degradation of cystic fibrosis transmembrane regulator (CFTR) by the endoplasmic reticulum associated degradation (ERAD) pathway and/or ubiquitin-proteasome pathway and/or the selective inhibition of cellular degradation of IκB the ubiquitin-proteasome pathway through the administration of a proteasome inhibitor.

In one aspect, the invention features an inhibitor of p97/valosin-containing protein which is capable of reducing cellular degradation of cystic fibrosis transmembrane regulator or IκB, wherein the inhibitor is selected from the group consisting of (a) an inhibitory nucleic acid molecule; (b) a small molecule inhibitor; and (c) a functional molecule inhibitor.

In another aspect, the present invention provides an inhibitory nucleic acid molecule that corresponds to or is complementary to at least a fragment of a nucleic acid molecule encoding a p97/valosin-containing protein that decreases p97/valosin-containing protein expression in a cell.

The present invention in another aspect provides an inhibitor of gp78 which is capable of reducing cellular degradation of cystic fibrosis transmembrane regulator or IκB, wherein the inhibitor is selected from the group consisting of: (a) an inhibitory nucleic acid molecule; (b) a small molecule inhibitor, and (c) a functional molecule inhibitor.

In a still further aspect of the invention, a method of treating an individual having a disorder is provided, said disorder characterized as having a IκB/NFκB-mediated chronic inflammatory response component, comprising the step of administering to said individual a therapeutically effective amount of an inhibitor of a p97/valosin-containing protein, wherein the inhibition of p97/valosin-containing protein alleviates the IκB/NFκB-mediated chronic inflammatory response component.

In yet another aspect, the present invention features a method of treating an individual having a disorder, said disorder comprising a IκB/NFκB-mediated chronic inflammatory response component, comprising the step of administering to said individual a therapeutically effective amount of a proteasome inhibitor, wherein the inhibition of the proteasome alleviates the IκB/NFκB-mediated chronic inflammatory response component.

In a still further aspect, the present invention provides a method of treating cystic fibrosis in an individual in need of such treatment, comprising the step of administering one or more inhibitors each of which is capable of reducing cellular degradation of cystic fibrosis transmembrane regulator or IκB, wherein the one or more inhibitors are selected from the group consisting of a p97/valosin-containing protein inhibitor, a gp78 inhibitor, and a proteasome inhibitor.

The present invention further provides in another aspect a pharmaceutical composition comprising a therapeutically effective dose of an inhibitor of p97/valosin-containing protein in accordance with the description herein, and one or more pharmaceutically acceptable non-active ingredients.

In another aspect, the present invention features a pharmaceutical composition comprising a therapeutically effective dose of an inhibitor of gp78 in accordance with the herein description, and one or more pharmaceutically acceptable non-active ingredients.

A further aspect of the present invention provides a kit comprising a therapeutically effective dose of an inhibitor of p97/valosin-containing protein in accordance with the herein description, and instructions for use thereof.

In still a further aspect, the present invention features a kit comprising a therapeutically effective dose of an inhibitor of gp78 in accordance with the herein description, and instructions for use thereof.

These and other embodiments are disclosed, or are obvious from and encompassed by, the following detailed description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 (A-C) demonstrates that inhibition of valosin-containing protein (VCP)/p97 expression results in accumulation of cystic fibrosis transmembrane receptor (CFTR) in the endoplasmic reticulum (ER). Panel (A) shows the results of an immunoblot. The total protein extract (10 μg) from freshly isolated bronchial epithelial cells obtained at bronchoscopy from position 508 phenylalanine deletion mutant (ΔF508) cystic fibrosis (CF) subjects and non-CF controls was immunoblotted for valosin-containing protein (VCP) and β-actin (as loading control). Valosin containing protein is over-expressed in CF airways. Panel (B) shows results of immunoblotting experiments (upper panel) and immunoflouresence studies (lower panel). IB3-1 cells were transfected with ΔF508-CFTR-GFP, and co-transfected with VCP shRNA (ΔVCP). The ΔVCP efficiency is shown in the upper panel where VCP protein level is drastically decreased by ΔVCP compared to the control lane (20 μg each lane). In a parallel experiment in the lower panel, the ΔF508-CFTR-GFP accumulates in a perinuclear location when VCP is decreased. Panel (C) shows the results of immunoflourescence experiments. IB3-1 cells were transfected with ΔF508-CFTR-GFP and/or ΔVCP were loaded with Endoplasmic Reticulum (ER)-tracker blue-white DPX dye. Localization of ΔF508-CFTR-GFP and ER tracker blue dye is shown in upper and middle panel. The lower panel shows the bright field image of the area indicating the normal morphology of cells after VCP inhibition. Co-localization of ER tracker blue dye and ΔF508-CFTR-GFP demonstrate the accumulation of ΔF508-CFTR in ER. VCP inhibition augment the ΔF508-CFTR accumulation in ER and part of it appears to escape from ER in ΔVCP IB3-1 cells. The bar indicated in the figure represents 20 μm.

FIG. 3 (A-C) shows that proteasome inhibition modulates VCP-cystic fibrosis transmembrane receptor immune complex. Panel (A) shows IB3-1 cells treated with bortezomib for 6 hrs, and immunoblotted for gp78, Hsp70, VCP, Hsp40 and β-actin. Bortezomib mediated proteasome modulation induced Hsp70 and inhibited VCP with no change in gp78 and Hsp40. Panel (B) shows cystic fibrosis transmembrane receptor (CFTR) immunoprecipitates from IB3-1 and S9 cells (500 µg/ml), immunoblotted for VCP (upper panel) and CFTR (lower panel, C and B forms). Panel (C) shows CFTR, pre-immune sera, VCP and Hsp40 immunoprecipitates from IB3-1 cells, immunoblotted for VCP. VCP co-immunoprecipitates wt-/ΔF508-CFTR, VCP and Hsp40. ΔF508-CFTR. (B-form); wild type CFTR mature (C-form).

FIG. 4 (A and B) demonstrates that VCP/p97 interacts with cystic fibrosis transmembrane receptor immune complex. In panel (A), VCP, pre-immune sera, CHIP, Hsp70, Hsc70, Hsp90, Hsp40 and CFTR were immunoprecipitated from IB3-1/S9 cells and then immunoblotted for VCP. VCP co-immunoprecipitates with both wt-/ΔF508-CFTR, moreover VCP selectively co-immunoprecipitates with Hsp90, Hsp70, Hsp40, Hsc70 and CHIP in presence of ΔF508-CFTR (IB3-1) as compared to wt-CFTR (S9). In panel (B), CFTR, CHIP, gp78, Hsp40, Hsc70, Hsp70 or Hsp90 were immunoprecipitated from bronchial brushing of ΔF508-CF subjects and immunoblotted for VCP or Hsc70. VCP and Hsc70 co-immunoprecipitates ΔF508-CFTR, Hsp70, Hsc70 and Hsp40 but not CHIP or gp78 from ΔF508 CF subjects.

FIG. 8 provides the nucleotide sequences of SEQ ID NO:1, SEQ ID NO: 2, SEQ ID NO: 3, SEQ ID NO: 4.

DETAILED DESCRIPTION OF THE INVENTION

Figure 2A:
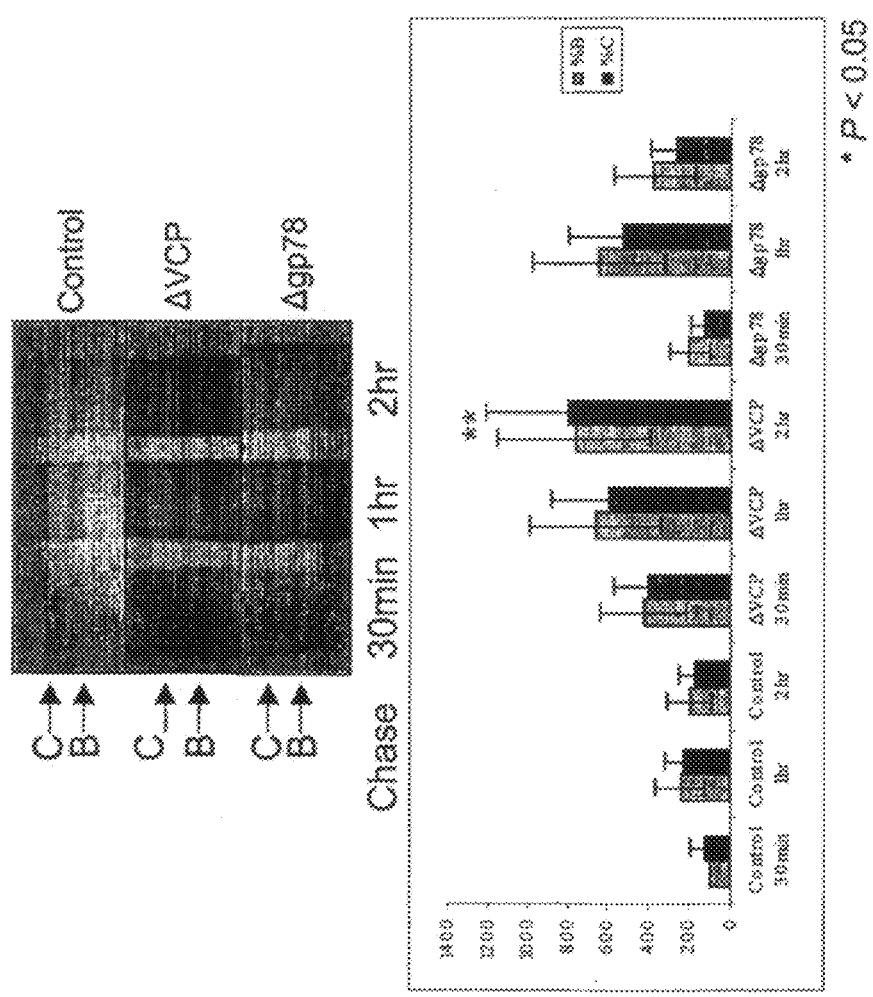
FIG. 2 (A-D) is a series of four graphs that shows VCP/p97 is involved in endoplasmic reticulum associated degradation of cystic fibrosis transmembrane receptor, and inhibition of VCP or proteasomal degradation by bortezomib can rescue CFTR. IB3-1 cells were transfected with ΔF508-CFTR for 48 hrs, metabolically labeled for 30 min with TRAN-35S-label, and chased for the indicated time points. The graphs on the bottom represent a quantitation of the results shown on the top. The ΔF508-CFTR was immunoprecipitated using rabbit polyclonal anti-CFTR 169 antibody. (A) shows IB3-1 cells transfected with ΔF508-CFTR and co-transfected with ΔVCP or Δgp78 for 48 hrs. VCP/gp78 inhibition results in accumulation of ΔF508-CFTR (B-form) and partial rescue of mature (C-form). (B) shows S9 cells transfected with wt-CFTR for 48 hrs or treated with 10 µM bortezomib for 6 hrs, 42 hrs post-transfection. Transfected cells were metabolically labeled for 30 min with TRAN-35S-label, and chased for the indicated time points. The wt-CFTR was immunoprecipitated using rabbit polyclonal anti-CFTR 169 antibody. VCP inhibition rescues the wild type-CFTR while proteasome modulation by bortezomib stabilizes the wild type-CFTR mature (C-form). Data are the mean±SD of three experiments. (C) shows CFTE cells transfected with ΔF508-CFTR. 42 hrs post-transfection cells were treated with 0 or 10 µM bortezomib for 6 hrs. Proteasome modulation by bortezomib rescues the ΔF508-CFTR mature (C-form) by 2 hrs. (D) shows IB3-1 cells transfected with the following: pCIneo, pSM2, pcDNA3, gp78ΔC, ΔHsp70, ΔVCP, Δgp78, VCPQQ for 48 hrs, or treated with 10 µM bortezomib for 6 hrs. Both VCP inhibition and proteasome modulation by bortezomib partially rescues the ΔF508-CFTR (B-form). Data in each right hand panel are the mean±SD of three experiments.

The present invention generally relates to a number of discoveries made by the present inventors stemming from their investigations into the degradation of mutant cystic fibrosis transmembrane regulators and the roles of the endoplasmic reticulum-associated protein degradation (ERAD) system and the ubiquitin-proteasome system in that process.

Certain cellular processes for protein degradation are known. In what is referred to as the "unfolded protein response" (UPS), protein degradation is carried out by essentially two steps. In the first step, the target protein is conjugated with multi-ubiquitin molecules, which mark the protein for destruction. In the second step, the target protein is transferred to the 26S proteasome, unfolded and degraded. P97/valosin-containing protein (sometimes designated herein as VCP) is a multi-ubiquitin chain-targeting factor that is required in degradation of numerous UPS substrates (24,25). VCP is known to interact with U-box domain containing protein Ufd2 and gp78 (ERAD related E3) resulting in ubiquitination of misfolded protein followed by retranslocation to the proteasome (8,26,27).

The present inventors have observed it is believed for the first time that inhibition of VCP leads to accumulation of CFTR in the endoplasmic reticulum (ER) and a portion of the rescued mutant CFTR traffics through to the Golgi. Parallel studies from other groups using yeast and mammalian systems demonstrated that CDC48NCP functions with the UFD1-NLP4 co-chaperone complex to bind ubiquitinated ERAD substrates and deliver them to proteasomes. The CDC48/VCP chaperone complex binds ubiquitinated misfolded proteins, such as, for example defective CFTR proteins, and assists in their delivery from Hsp70 and Hsp90 to the proteasome (28,29). The NSF (N-ethyl maleimide sensitive factor) and VCP are related AAA ATPase proteins implicated in membrane trafficking and organelle biogenesis. Although, it was recently reported that VCP does not affect membrane trafficking (30), the present inventors observed that partial CFTR rescue by VCP inhibition indicate the following possibilities: (a) that a small proportion of endogenous VCP can support membrane trafficking function of specific proteins but not ERAD; (b) NSF or other related membrane trafficking components become active in response to accumulation of protein(s) in ER; or (c) VCP inhibition may rescue trafficking proteins from proteasome mediated degradation.

Two representative mammalian U-box proteins, Ufd2 and CHIP, interact with the molecular chaperones VCP and either Hsp90 or Hsc70, respectively and are implicated in the degradation of damaged proteins (31). The combination of CHIP with Hsp90 mediates ubiquitylation of the glucocorticoid receptor, and CHIP together with Hsc70 is known to target immature CFTR for proteasomal degradation (32,33). The present inventors demonstrated it is believed for the first time that VCP is directly associated with CFTR and is a requisite for ERAD of CFTR.

Inhibition of proteasome activity by N-acetyl-leucylleucyl-Norleucinal (ALLN) (10 mg/ml) blocks ΔF508-CFTR it degradation and drives the accumulation of ubiquitinated forms of ΔF508-CFTR in Triton X-100-insoluble aggregates (34). It was recently reported that inhibition of the proteasome leads polyubiquitinated ΔF508-CFTR to aggregate because it can be extracted from the ER membrane by the VCP-UFD1-NPL4 complex (7), but cannot be degraded by the proteasome (34). On the other hand, the non-ubiquitinated ΔF508-CFTR that accumulates in response to inhibition of the Hsp70-CHIP E3 does not aggregate because it is inserted into the ER membrane and is bound by cytosolic Hsc70. Thus, while ΔF508-CFTR has a folding defect that prevents it from passing quality control and escaping the ER, it does not appear to be overly aggregation prone and cellular chaperones can maintain it in a foldable state (35). The nature of the folding defect of ΔF508-CFTR and what causes it to be selected for proteasomal degradation is not completely clear. To block the VCP mediated proteasomal degradation of CFTR we used bortezomib. The inventors showed that proteasome inhibition with bortezomib or VCP inhibition partially rescued mature ΔF508-CFTR in IB3-1 cells. Bortezomib induced Hsp70 and down-regulated VCP protein expression. A recent report also demonstrated the inhibition of VCP by another proteasome inhibitor, heroin (36). Proteasome inhibition may also rescue trafficking protein(s) from degradation that may be involved in ΔF508-CFTR rescue to cell surface.

The present inventors have also shown for the first time that bortezomib can rescue ΔF508-CFTR from ERAD resulting in the appearance of mature CFTR. A main concern in considering the proteasome as a therapeutic target is the theoretical risk that multiple processes may be affected by proteasome inhibitors. ERAD is a central element of the secretory pathway and has major implications for the generation of various human diseases. ERAD was originally thought to exclusively degrade inefficiently folded and orphan secretory proteins. It is becoming clear that ERAD has important consequences for diverse aspects of cell physiology, including protein folding and transport, metabolic regulation, immune response and ubiquitin-proteasome-dependent degradation (2). The inventors have further observed that the risk of global suppression of proteasomal degradation may be balanced by the favorable anti-inflammatory effect observed.

Several studies have indicated that pulmonary inflammation may occur early in the course of CF, although the existence of primary inflammation is controversial (42,43). It has been shown that human bronchial epithelial cells expressing ΔF508-CFTR generate more IL8 in response to TNFα, IL1-β or P. aeruginosa (21). These studies indicate that neutrophilic association with increased IL8 in the airways is a prominent early feature of CF and suggest the exuberant airway inflammation is a component of the CF phenotype. In quiescent cells, nuclear factor IκB (NFκB) is sequestered to cytoplasm by its interaction with a member of the inhibitory IκB family that includes IκB-α and IκB-β. After cell stimulation, IκB-α is phosphorylated, polyubiquitinated and degraded by 26S proteasome activity. IκB-α degradation unmasks nuclear localization signals that allow NFκB to be transported to the nucleus resulting in activation of IL8 gene transcription (23).

The present inventors further discovered that VCP inhibition in the presence of bortezomib significantly inhibited IL1-β-induced IL8 cytokine levels in cells. Without meaning to be bound by theory, the present inventors discovered that VCP is an integral component of ERAD and ER stress pathways induced by UPR in CF, and may be central to the efficacy of CF drugs that target the ubiquitin proteasome system. Modulating proteasomal degradation by bortezomib or VCP shRNA rescues the functional mutant CFTR to the cell surface and suppresses NFκB mediated IL8 activation. This ability to ameliorate secondary aspects of CF disease pathophysiology in addition to rescue of CFTR to the cell surface is promising for CF therapeutics. Moreover, selective modulation of ERAD components can be a potential therapeutic for a wide range of human diseases associated with ERAD.

It is emphasized that any of the particular discoveries made by the present inventors as described above are not meant to limit the invention in any way.

Accordingly, the present invention as supported by the above discoveries broadly relates to compositions and methods of using the compositions in the treatment of disorders and/or diseases involving the ERAD pathway, the ubiquitin-proteasome pathway, or the IκB/NFκB-mediated chronic inflammatory response. As noted above, it has been surprisingly discovered that inhibiting the interaction between p97NCP and gp78 is a viable way to reduce the degradation of CFTR proteins by the ERAD pathway and/or the ubiquitin-proteasome pathway, and accordingly, a viable way to restore or promote functional calcium channels in cells and further, a viable approach to treating cystic fibrosis or a symptom thereof. In addition, it as has been surprisingly discovered that inhibiting the interaction between p97NCP and IκB is a viable way to reduce or block the degradation of IκB by the ubiquitin-proteasome pathway, and thus, maintain or promote the inhibition of the IκB/NFκB-mediated chronic inflammatory response. Further, it has been surprisingly discovered that inhibiting the ubiquitin-proteasome pathway can reduce the intracellular degradation of one or both of CFTR and IκB, and thus, provide a viable way to treat cystic fibrosis and/or a disorder or disease having a IκB/NFκB-mediated chronic inflammatory response component. Further still, it has been surprisingly discovered that one or more inhibitors of p97NCP, gp78 and/or the ubiquitin-proteasome pathway can be administered in combination or at about the same time to synergistically treat cystic fibrosis and/or a disease or disorder having a IκB/NFκB-mediated chronic inflammatory response component.

Thus, the present invention generally provides methods and compounds for treating a disorder and/or condition that involves the endoplasmic reticulum associated degradation (ERAD) pathway and/or the ubiquitin-proteasome system and/or which can be characterized as having a IκB/NFκB-mediated chronic inflammatory response (e.g. cystic fibrosis). The present invention especially relates to compositions and methods for selectively inhibiting cellular degradation of cystic fibrosis transmembrane regulator (CFTR) by the ERAD pathway and/or ubiquitin-protease system through the blocking of interactions between p97/valosin-containing protein and/or gp78 with CFTR. The present invention further relates to composition and methods for selectively inhibiting cellular degradation of IκB by the ubiquitin-proteasome system, and thus, maintaining and/or promoting the inhibition of the IκB/NFκB-mediated chronic inflammatory response, through blocking and/or minimizing interactions between p97/valosin-containing protein and IκB. The invention further relates to the selective inhibition of cellular degradation of cystic fibrosis transmembrane regulator (CFTR) by the ERAD pathway and/or ubiquitin-proteasome pathway and/or the selective inhibition of cellular degradation of IκB the ubiquitin-proteasome pathway through the administration of a proteasome inhibitor.

Definitions

Unless defined otherwise, all technical and scientific terms used herein have the meaning commonly understood by one of ordinary skill in the art to which this invention belongs. The following references can provide one of skill in the art to which this invention pertains with a general definition of many of the terms used in this invention, and can be referenced and used so long as such definitions are consistent the meaning commonly understood in the art: Singleton et al., Dictionary of Microbiology and Molecular Biology (2d ed. 1994); The Cambridge Dictionary of Science and Technology (Walker ed., 1988); Hale & Marham, The Harper Collins Dictionary of Biology (1991); and Lackie et al., The Dictionary of Cell & Molecular Biology (3d ed. 1999); and Cellular and Molecular Immunology, Eds. Abbas, Lichtman and Pober, $2^{nd}$ Edition, W.B. Saunders Company. Any additional technical resources available to the person of ordinary skill in the art providing definitions of terms used herein having the meaning commonly understood in the art can be consulted.

For the purposes of the present invention, the following terms are further defined. Additional terms are defined elsewhere in the description.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "administration" or "administering" is meant to include an act of providing a compound or pharmaceutical composition of the invention to a subject in need of treatment.

By "cells," or "host cells" are meant terms that are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. The term is meant to include any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

By "complementary" is meant capable of pairing to form a double-stranded nucleic acid molecule or portion thereof. In one embodiment, an inhibitory nucleic acid molecule is in large part complementary to a target sequence. The complementarity need not be perfect, but may include mismatches at 1, 2, 3, or more nucleotides.

By "corresponds" is meant comprising at least a fragment of a double-stranded gene, such that a strand of the double-stranded inhibitory nucleic acid molecule is capable of binding to a complementary strand of the gene.

By "cystic fibrosis transmembrane receptor" (CFTR) is meant a cAMP-regulated chloride channel expressed at the apical membrane of epithelial cells in the airways, pancreas, testis, and other tissues. A mutant CFTR can mean, for example, a CFTR receptor that is defective in protein folding, stability, and/or channel gating.

By "C/EBP-homologous protein (CHOP)" (C/EBP-homologous protein (CHOP)) is meant to include a C/EBP family transcription factor which is involved in endoplasmic reticulum (ER) stress-mediated apoptosis. By convention, the term "CHOP" refers to an C/EBP-homologous protein gene whereas the term "CHOP" refers to a C/EBP-homologous protein gene product, respectively. An exemplary CHOP sequence is specified by Reference Sequence NM_004083.

By "conditions having a IκB/NFκB-mediated chronic inflammatory response," or a similarly worded expression, is meant diseases or conditions characterized by a prominent neutrophilic invasion, typically involving the sinuses, upper airways, lower airways and/or any organ with exocrine gland secretory component such as intestines, e.g., Crohn's disease, but also arising in parts of the body without glands such as central nervous system, skin, joints. Exemplary conditions include, but are not limited to, cystic fibrosis, forms of diabetes insipidus, type II diabetes, Parkinson's Disease, Alzheimer's Disease, amyloidosis, surfactant protein C deficiency, ABCA3 deficiency, Huntington's Disease, adrenoleukodystrophy, amyotrophic lateral sclerosis, retinitis pigmentosa, polyglutamine diseases, mad cow disease, alpha one antitrypsin deficiency, short chain acyl CoA dehydrogenase deficiencies inclusion body myositis aging, chronic inflammatory diseases, chronic obstructive pulomonary disorder, chronic bronchitis, chronic sinusitis, chronic inflammatory conditions, inflammatory bowel diseases, including ulcerative colitis and crohn's disease.

By "decrease" is meant a negative alternative. For example, a reduction by at least about 5% relative to a reference level. An exemplary decrease may be by 5%, 10%, 15%, 20%, 25% or 50%, or even by as much as 75%, 85%, 95% or more.

By "effective dose" or "effective amount" is meant the amount of an agent required to ameliorate the symptoms of a disease relative to an untreated patient. The effective amount of active agent(s) used to practice the present invention for therapeutic treatment of a cystic fibrosis varies depending upon the manner of administration, the age, body weight, and general health of the subject. Ultimately, the attending physician or veterinarian will decide the appropriate amount and dosage regimen. Such amount is referred to as an "effective" amount.

By "endoplasmic reticulum-associated degradation" is meant the process in which proteins that fail to fold properly as well as constitutive or regulated short-lived proteins of the endoplasmatic reticulum (ER) are subjected to proteolysis by cytosolic 26 S proteasomes. Endoplasmic reticulum-associated protein degradation (ERAD) eliminates misfolded, damaged, or mutant proteins with abnormal conformation.

By "fluids" or "body fluids" is meant a biological fluid sample from an individual. Fluids or body fluids are taken from an individual, and can be serum or blood. Serum or blood can be used in a diagnostic test to determine amount of agent or therapeutic agent in an individual. For example, a therapeutically effective amount of an inhibitor can be the amount that is effective to establish a concentration of the inhibitor in body fluids.

By "functional inhibitor" is meant an agent that decreases, suppresses, attenuates, diminishes, arrests, or stabilizes the activity of a molecule. For example, an agent that reduces biological activity, e.g. enzyme activity, tyrosine kinase activity.

By "fragment" is meant a portion (e.g., at least 10, 25, 50, 100, 125, 150, 200, 250, 300, 350, 400, or 500 amino acids or nucleic acids) of a protein or nucleic acid molecule that is substantially identical to a reference protein or nucleic acid and retains the same or substantially the same biological activity of the reference. For example, an inhibitory nucleic acid molecule of the invention can correspond to at least a fragment of a p97/valosin-containing protein nucleic acid molecule that decreases p97/valosin-containing protein expression in a cell.

By "gp78" (gp78) is meant to include a RING finger-dependent ubiquitin protein ligase of the endoplasmic reticulum (ER). By convention, the term "gp78" refers to the gene whereas the term "gp78" refers to the gene product, respectively. An exemplary gp78 sequence is specified by Reference Sequence NM_001144.

By or "identity" "homology" or "similarity" is meant to refer to sequence similarity between between two nucleic acid molecules, or two peptides, with identity being a more strict comparison. Homology and identity can each be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. An "unrelated" or "non-homologous" sequence shares less than 40% identity, though preferably less than 25% identity, with one of the sequences of the present invention.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. 70-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases. Databases with individual sequences are described in Methods in Enzymology. ed. Doolittle, supra. Databases include Genbank, EMBL, and DNA Database of Japan (DDBJ).

Preferred nucleic acids have a sequence at least about 70%, and more preferably at least about 75% identical and even more preferably at least about 85% identical to an nucleic acid sequence of a sequence shown in one of SEQ ID NOS: 1 or 2.

By "individual" is intended to include vertebrates, preferably a mammal. Mammals include, but are not limited to, humans.

By "inhibitor" is meant an agent that decreases, suppresses, attenuates, diminishes, arrests, or stabilizes the development or progression of a disease.

By "inhibitory nucleic acid molecule" is meant a single stranded or double-stranded RNA, siRNA (short interfering RNA), shRNA (short hairpin RNA), or antisense RNA, or a portion thereof, or an analog or mimetic thereof, that when administered to a mammalian cell results in a decrease (e.g., by 10%, 25%, 50%, 75%, or even 90-100%) in the expression of a target sequence. Typically, a nucleic acid inhibitor comprises or corresponds to at least a portion of a target nucleic acid molecule, or an ortholog thereof, or comprises at least a portion of the complementary strand of a target nucleic acid molecule.

By "modification" is meant any biochemical or other synthetic alteration of a nucleotide, amino acid, or other agent relative to a naturally occurring reference agent.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases.

By "obtaining" as in "obtaining the inhibitory nucleic acid molecule" is meant synthesizing, purchasing, or otherwise acquiring the inhibitory nucleic acid molecule.

By "operably linked" is meant that a first polynucleotide is positioned adjacent to a second polynucleotide that directs transcription of the first polynucleotide when appropriate molecules (e.g., transcriptional activator proteins) are bound to the second polynucleotide. The term "pharmaceutically acceptable carrier" or "pharmaceutically acceptable excipient" is meant to refer to a carrier for administration of a therapeutic agent, such as an inhibitory nucleic acid, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles.

By "proteasome inhibitor" is meant any agent that inhibits, decreases, blocks or otherwise reduces the activity or expression of the proteasome. The proteasome is an enzyme complex that primarily functions in the degradation of misfolded proteins and is essential for the regulation of the cell cycle. Proteasomes are localized in the nucleus and cytosol, where they are largely associated with centrosomes, the cytoskeleton, and the outer endoplasmic reticulum. The form of the proteasome inhibitor can be any suitable form, such as, an inhibitory nucleic acid molecule, a small molecule inhibitor, or a functional molecule inhibitor. The inhibitor can target one or more subunits comprising the proteasome or a proteasome related gene.

By "siRNA" is meant to refer to small interfering RNA. SiRNA can be used in a method of RNA interference. A siRNA is a double stranded RNA that "corresponds" to or matches a reference or target gene sequence. This matching need not be perfect so long as each strand of the siRNA is capable of binding to at least a portion of the target sequence. SiRNA can be used to inhibit gene expression, see for example Bass, 2001, Nature, 411, 428 429; Elbashir et al., 2001, Nature, 411, 494 498; and Zamore et al., Cell 101:25-33 (2000).

By "shRNA" is meant short hairpin RNA. ShRNA can be used in a method of RNA interference. The term refers to a short sequence of RNA which makes a tight hairpin turn and can be used to silence or inhibit gene expression.

By "small molecule" as used herein, is meant to refer to a composition, which has a molecular weight of less than about 5 kDa and most preferably less than about 4 kDa. Small molecules can be nucleic acids, peptides, polypeptides, peptidomimetics, carbohydrates, lipids or other organic (carbon-containing) or inorganic molecules.

By "substantially identical" is meant a protein or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and still more preferably 90%, 95% or even 99% identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{100}$ indicating a closely related sequence.

By "target" or "targets" is meant alters the biological activity of a target polypeptide or nucleic acid molecule. Targets according to the invention can be p97/valosin containing protein, proteasome, or gp78.

By "valosin containing protein" (VCP) is meant to include a 97 kDa protein belonging to the family of AAA ATPases. Cdc 48 is the yeast counterpart of the mammalian VCP protein. VCP proteins participate in the retrograde translocation of misfolded proteins from the ER for degradation by the cytosolic proteasomes. By convention, the term "VCP" refers to the gene whereas the term "VCP" refers to the gene product, respectively. An exemplary VCP sequence is specified by Reference Sequence NM_007126. As expressed herein, VCP may equivalently by designated as "p97/valosin-containing protein," or "(VCP)/p97" or the like.

By "vector" is meant a nucleic acid molecule, for example, a plasmid, cosmid, or bacteriophage, that is capable of replication in a host cell. In one embodiment, a vector is an expression vector that is a nucleic acid construct, generated recombinantly or synthetically, bearing a series of specified nucleic acid elements that enable transcription of a nucleic acid molecule in a host cell. Typically, expression is placed under the control of certain regulatory elements, including constitutive or inducible promoters, tissue-preferred regulatory elements, and enhancers.

Endoplasmic Reticulum Associated Degradation (ERAD)

The endoplasmic reticulum (ER) is the eukaryotic organelle where most secretory proteins are folded for subsequent delivery to their site of action. Correct folding of newly synthesized proteins is ensured by an ER quality control system called ER-associated protein degradation (ERAD) (56). This system also controls the degradation of constitutive or regulated short-lived proteins of the ER. This ERAD system recognizes misfolded, damaged, mutant or unassembled proteins and prevents them from reaching their final destination. Instead, they are extracted from the ER, polyubiquitinated and degraded by the cytosolic proteasome, also named the cytoplasmic ubiquitin-proteasome system (UPS). UPS plays a pivotal role in cell homeostasis and is vital in regulating various cellular processes. In normal cells, nearly all proteins are continuously degraded and replaced by de novo synthesis. The spatial separation between substrate selection and degradation in ERAD requires substrate transport from the ER to the cytoplasm by a process termed dislocation; recently reviewed by Meusser et al. (2).

The ubiquitin-proteasome system consists of two steps: first, the target protein is conjugated with multi-ubiquitin (Ub) molecules, which mark the substrate for destruction; second, the target protein is transferred to the 26S proteasome, unfolded and degraded. Valosin consisting of protein (VCP) is a multi-ubiquitin chain-targeting factor that is required in degradation of numerous UPS substrates (24,25). VCP is known to interact with other proteins, such as gp78, resulting in the ubiquitination of misfolded proteins, followed by retranslocation to the proteasome (8,26,27).

Proteins that are unable to fold correctly cause ER stress and activate the unfolded protein response (UPR). The proteasome contributes to ERAD by relieving the ER stress. The accumulation of unfolded protein within the lumen of the ER leads to prolonged UPR activation, which in turn causes oxidative stress which can lead ultimately to cell death (47). ERAD is a central element of the secretory pathway and has major implications for the generation of various human diseases. While ERAD was once thought to exclusively degrade inefficiently folded and orphan secretory proteins, it is becoming clear that ERAD has important consequences for diverse aspects of cell physiology, including protein folding and transport, metabolic regulation, immune response and ubiquitin-proteasome-dependent degradation (2). Although a risk of global suppression of proteasomal degradation may be considered, this potential risk can be balanced by a potentially favorable anti-inflammatory effect.

Valosin-Containing Protein

The 97-kDa valosin-containing protein (p97 or VCP or p97NCP; Cdc48 in yeast) is a type-II $AAA^+$ protein. The $AAA^+$ gene family are ATPases associated with diverse cellular activities, and are characterized by conserved 200-250 residues that include Walker A and B motifs. The most common function of $AAA^+$ domain is to catalyze protein folding or unfolding in an ATP-dependent manner. All known $AAA^+$ proteins contain either 1 or 2 $AAA^+$ domains, and the family can be divided into 2 groups on this basis.

VCP forms a stable homo-hexameric structure, and this two-tier ring-shaped complex acts as a molecular chaperone that mediates many seemingly unrelated cellular activities. One of the most well-examined roles of VCP involves endoplasmic reticulum associated degradation, wherein resident and transient ER proteins can be selectively or constitutively degraded in the cytoplasm by the ubiquitin proteasome system (Tsai et al., 2002; Meusser et al., 2005; Romisch, 2005; Bar-Nun, 2005).

Mammalian p97/VCP (valosin containing protein) and Cdc48, participate in retrograde translocation of misfolded proteins from the ER for degradation by the cytosolic proteasomes (6). The p97/VCP and its cofactors (e.g., Ufd1, Np14 and p47) interact with misfolded ubiquitinated substrates to dislodge them from the ER to the cytosol for proteasomal degradation (7). The most common mutation in cystic fibrosis (Δ508-CFTR) is located in first $AAA^+$ domain (amino acid 508), resulting in misfolding and subsequent degradation of CFTR.

Gp78 was originally identified as tumor autocrine motility factor (AMFR), and is a multi-spanning membrane protein with RING-finger-type ubiquitin protein ligase activity exposed to the cytoplasmic ER surface. Expression of gp78 has been correlated with tumor metastasis. VCP/p97 physically interacts with gp78 to couple ubiquitination, retro-translocation and proteasomal degradation (8). AMFR/gp78 is thus distinguished from CHIP and Parkin ubiquitin protein ligases and closely resembles the yeast ERAD E3 ligase Hrd1p/Der3p. In yeast, Hrd1p/Der3p and Cdc48 are required for CFTR degradation (9).

Cystic Fibrosis

Cystic fibrosis (CF) is one of the most common inherited diseases, afflicting 1 in approximately 2,500 white individuals (50). The primary cause of morbidity and mortality in CF is chronic lung infection and deterioration of lung function. CF is caused by mutations in the CF transmembrane conductance regulator (CFTR) gene, which encodes a cAMP-regulated chloride channel expressed at the apical membrane of epithelial cells in the airways, pancreas, testis, and other tissues (51, 52). The most common CFTR mutation producing CF is deletion of phenylalanine at residue 508 (ΔF508) in its amino acid sequence, which is present in at least 1 allele in approximately 90% of CF subjects (50). The ΔF508-CFTR protein is misfolded and retained at the ER, where it is degraded rapidly (53, 54). When allowed to traffic out of the ER by overexpression or by low-temperature incubation, ΔF508-CFTR also has a reduced half-life in the plasma membrane compared with wild-type CFTR (55). In general, nonsense or stop mutations in CFTR result in severe disease because of a lack of plasma-membrane CFTR.

Cystic Fibrosis-Associated Immune Response

Several studies have indicated that pulmonary inflammation may occur early in the course of CF, although the existence of primary inflammation is controversial (42,43). It has been shown that human bronchial epithelial cells expressing ΔF508-CFTR generate more IL8 in response to TNFα, IL1-β or P. aeruginosa (21). These studies indicate that neutrophilic association with increased IL8 in the airways is a prominent early feature of CF and suggest the exuberant airway inflammation is a component of the CF phenotype. In quiescent cells, NFκB is sequestered to cytoplasm by its interaction with a member of the inhibitory IκB family that includes IκB-α and IκB-β. After cell stimulation, IκB-α is phosphorylated, polyubiquitinated and degraded by 26S proteasome activity. IκB-α degradation unmasks nuclear localization signals that allow NRB to be transported to the nucleus resulting in activation of IL8 gene transcription (23). VCP physically associates with IκBα and the 26S proteasome, and targets IκBα to the proteasome for degradation (16).

Inhibitory Nucleic Acid Molecules

The invention provides in one aspect compositions that inhibit p97/vasolin-containing protein (VCP) as well as gp78, a VCP partner, and methods of using such compositions for the treatment of various diseases. In one embodiment, the invention provides inhibitory nucleic acid molecules, such as antisense nucleic acid molecules, that decrease the expression of a target protein, such as, p97/VCP or gp78. In another embodiment, the invention provides inhibitory nucleic acid molecules, such as antisense nucleic acid molecules, that decrease the expression of gp78.

As used herein, antisense therapy refers to administration or in situ generation of oligonucleotide molecules or their derivatives which specifically hybridize (e.g., bind) under cellular conditions with the cellular mRNA and/or genomic DNA, thereby inhibiting transcription and/or translation of that gene. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide sequences.

An antisense construct can be delivered, for example, as an expression plasmid which, when transcribed in the cell, produces RNA which is complementary to at least a unique portion of the cellular mRNA. Alternatively, the antisense construct is an oligonucleotide probe which is generated ex vivo and which, when introduced into the cell, causes inhibition of expression by hybridizing with the mRNA and/or genomic sequences of a subject nucleic acid. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668. With respect to antisense DNA, oligodeoxyribonucleotides derived from the translation initiation site, e.g., between the −10 and +10 regions of the nucleotide sequence of interest, are preferred.

Antisense approaches involve the design of oligonucleotides (either DNA or RNA) that are complementary to nRNA. The antisense oligonucleotides will bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

The antisense molecules provided by the invention include any inhibitory nucleic acid molecule sufficient to decrease the expression of a nucleic acid molecule, for example a nucleic acid molecule of p97/VCP by at least 5-10%, desirably by at least 25%-50%, or even by as much as 75%-100%. The antisense nucleic acid molecules provided by the invention also include any nucleic acid molecule sufficient to decrease the expression of a nucleic acid molecule of gp78 by at least 5-10%, desirably by at least 25%-50%, or even by as much as 75%-100%. Each of the nucleic acid sequences provided herein may be used, for example, in the discovery and development of therapeutic antisense nucleic acid molecules to decrease the expression of p97/VCP or gp78. If desired, antisense nucleic acid molecules that target p97/VCP and gp78 are administered in combination, such that the coordinated reduction in the expression of p97/VCP and gp78 is achieved.

The invention is not limited to antisense nucleic acid molecules but encompasses virtually any single-stranded or double-stranded nucleic acid molecule that decreases expression of p97/VCP or gp78. Thus, the invention can further provide catalytic RNA molecules or ribozymes. Such catalytic RNA molecules can be used to inhibit expression of p97/VCP or gp78 nucleic acid molecule in vivo.

The inclusion of ribozyme sequences within an antisense RNA confers RNA-cleaving activity upon the molecule, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference. In various embodiments of this invention, the catalytic nucleic acid molecule is formed in a hammerhead or hairpin motif. Examples of such hammerhead motifs are described by Rossi et al., Nucleic Acids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In another approach, the inhibitory nucleic acid molecule is a double-stranded nucleic acid molecule used for RNA interference (RNAi)-mediated knock-down of the expression of p97/VCP or gp78. siRNAs are also useful for the inhibition of p97/VCP or gp78. See, for example, Nakamoto et al., Hum Mol Genet, 2005. Desirably, the siRNA is designed such that it provides for the cleavage of a target protein, e.g. p97/VCP or gp78, of the invention.

In one embodiment, a double-stranded RNA (dsRNA) molecule is made that includes between eight and twenty-five (e.g., 8, 10, 12, 15, 16, 17, 18, 19, 20, 21, 22, 23, 24, 25) consecutive nucleobases of a nucleobase oligomer of the invention. The dsRNA can be two complementary strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. Double stranded RNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference. An inhibitory nucleic acid molecule that "corresponds" to p97/VCP or "corresponds" to gp78 comprises at least a fragment of the double-stranded gene, such that each strand of the double-stranded inhibitory nucleic acid molecule is capable of binding to the complementary strand of the target gene. The inhibitory nucleic acid molecule need not have perfect correspondence or need not be perfectly complementary to the reference sequence. In one embodiment, an siRNA has at least about 85%, 90%, 95%, 96%, 97%, 98%, or even 99% sequence identity with the target nucleic acid. For example, a 19 base pair duplex having 1-2 base pair mismatch is considered useful in the methods of the invention. In other embodiments, the nucleobase sequence of the inhibitory nucleic acid molecule exhibits 1, 2, 3, 4, 5 or more mismatches.

Inhibitory nucleic acid molecules of the invention also include double stranded nucleic acid "decoys." Decoy molecules contain a binding site for a transcription factor that is responsible for the deregulated transcription of a gene of interest. Thus, present invention can provide decoys that competitively block binding to a regulatory element in a target gene (e.g., p97/VCP or gp78). An overview of decoy technology is provided by Suda et al., Endocr. Rev., 1999, 20, 345-357; S. Yla-Herttuala and J. F. Martin, The Lancet 355, 213-222, 2000). In one therapeutic method, short double-stranded DNA decoy molecules are introduced into cells (e.g., neoplastic cells) of a subject. The decoys are provided in a form that facilitates their entry into target cells of the subject. Having entered a cell, the decoy specifically binds an endogenous transcription factor, thereby competitively inhibiting the transcription factor from binding to an endogenous gene. The decoys are administered in amounts and under conditions whereby binding of the endogenous transcription factor to the endogenous gene is effectively competitively inhibited without significant host toxicity. Depending on the transcription factor, the methods can effect up- or down-regulation of gene expression. The subject compositions comprise the decoy molecules in a context that provides for pharmacokinetics sufficient for effective therapeutic use.

In one embodiment, the inhibitory nucleic acid molecules of the invention are administered systemically in dosages between about 0.1 mg/kg and 100 mg/kg (e.g., 0.1, 0.5, 0.75, 1, 5, 10, 20, 25, 50, 75, and 100 mg/kg). Desirably, a human patient having a disease or condition characterized by a IκB/NFκB-mediated chronic inflammatory response, for example, cystic fibrosis, receives a dosage that is sufficient to establish a concentration of the inhibitor in body fluids an between about 1 nM to about 10 mM (e.g., 1 nm, 5 nm, 10 nm, 50 nm, 75 nm, 100 nm, 150 nm, 200 nm, 300 nm, 400 nm, 500 nm, 550 nm, 700 nm, 750 nm, 800 nm, 900 nm, 1000 nm, 1100 nm, 1200 nm, 1250 nm, 1500 nm, 2000 nm, 5000 nm, 10 000 nm).

Modified Inhibitory Nucleic Acid Molecules

A desirable inhibitory nucleic acid molecule is one based on 2'-modified oligonucleotides containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_{50}$. This modification also increases the nuclease resistance of the modified oligonucleotide. It is understood that the methods and reagents of the present invention may be used in conjunction with any technologies that may be developed to enhance the stability or efficacy of an inhibitory nucleic acid molecule.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO 88/09810, published Dec. 15, 1988) or the blood-brain barrier (see, e.g., PCT Publication No. WO 89/10134, published Apr. 25, 1988), hybridization-triggered cleavage agents (See, e.g., Krol et al., 1988, BioTechniques 6:958-976), or intercalating agents (See, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

Inhibitory nucleic acid molecules include nucleobase oligomers containing modified backbones or non-natural internucleoside linkages. Oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers. Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates, thionophosphoramidates, thionoalkylphosphonates, thionoallcylphosphotriesters, and boranophosphates. Various salts, mixed salts and free acid forms are also included. Representative United States patents that teach the preparation of the above phosphorus-containing linkages include, but are not limited to, U.S. Pat. Nos. 3,687,808; 4,469,863; 4,476, 301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Nucleobase oligomers may also contain one or more substituted sugar moieties. Such modifications include 2'-O-methyl and 2'-methoxyethoxy modifications. Another desirable modification is 2'-dimethylaminooxyethoxy, 2'-aminopropoxy and 2'-fluoro. Similar modifications may also be made at other positions on an oligonucleotide or other nucleobase oligomer, particularly the 3' position of the sugar on the 3' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873;

5,646,265; 5,658,873; 5,670,633; and 5,700,920, each of which is herein incorporated by reference in its entirety.

In other nucleobase oligomers, both the sugar and the internucleoside linkage, i.e., the backbone, are replaced with novel groups. The nucleobase units are maintained for hybridization with a nucleic acid molecule that codes for p97/VCP or gp78. Methods for making and using these nucleobase oligomers are described, for example, in "Peptide Nucleic Acids (PNA): Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In other embodiments, a single stranded modified nucleic acid molecule (e.g., a nucleic acid molecule comprising a phosphorothioate backbone and 2'-O-Me sugar modifications is conjugated to cholesterol. Such conjugated oligomers are known as "antagomirs."

Delivery of Nucleobase Oligomers

The inhibitory nucleic acid molecules in accordance with the invention can be delivered by any suitable means, including any suitable gene-therapy based delivery method or approach for delivering a nucleic acid to a cell and/or tissue under in vivo, ex vivo, or in vitro conditions. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

Naked oligonucleotides are capable of entering cells and inhibiting the expression of p97/vasolin containing protein or gp78. Nonetheless, it may be desirable to utilize a formulation that aids in the delivery of an inhibitory nucleic acid molecule or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Polynucleotide Therapy

Polynucleotide therapy featuring a polynucleotide encoding an inhibitory nucleic acid molecule or analog thereof that targets p97/vasolin containing protein or gp78 is another therapeutic approach for treating a disease in a subject. Expression vectors encoding inhibitory nucleic acid molecules can be delivered to cells of a subject. The nucleic acid molecules must be delivered to the cells of a subject in a form in which they can be taken up and are advantageously expressed so that therapeutically effective levels can be achieved.

Nucleic acid molecules and constructs providing transgenes such as antisense oligonucleotides under the control of highly cell-type specific promoters and amplification promoter elements, can be incorporated into a vector and administered to any mammal, including a human. Many such vectors are commercially available, and other suitable vectors can be readily prepared and obvious to the skilled artisan. The exact design of the vector depends on such factors as the choice of the host cell to be transformed and/or the type of protein desired to be expressed. Suitable vectors can be produced by ligating the desired construct into a plasmid or viral vector suitable for expression in eukaryotic cells (see, for example, Broach, et al., Experimental Manipulation of Gene Expression, ed. M. Inouye (Academic Press, 1983) p. 83; Molecular Cloning: A Laboratory Manual, 2nd Ed., ed. Sambrook, et al. (Cold Spring Harbor Laboratory Press, 1989) Chapters 16 and 17, the entireties of which are incorporated by reference herein).

Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding an inhibitory nucleic acid molecule can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77 S-83S, 1995). Examples of vectors that can be used include, but are not limited to, plasmids such as pBR322, pUC, or Co1E1; adenovirus; Sindbis virus; simian virus 40; cytomegalovirus; and retroviral vectors such as murine sarcoma virus, mouse mammary tumor virus, Moloney murine leukemia virus, and Rous sarcoma virus. Bacterial vectors can be used, such as *Salmonella* ssp., *Yersinia enterocolitica*, *Shigella* spp., *Vibrio cholerae, Mycobacterium* strain BCG, and *Listeria monocytogenes*. Minichromosomes such as MC and MCI, bacteriophages, cosmids (plasmids into which phage lambda cos sites have been inserted) and replicons (genetic elements that are capable of independent extrachromosomal replication).

To improve incorporation into the genome of the target cell (if desired), a retroviral vector can be used, and long terminal repeat (LTR) sequences can be added on either side of the expression construct (see, e.g., Vile, et al., Virology 214: 307-313 (1995), the entirety of which is incorporated by reference herein). Retroviral vectors are particularly well developed and have been used in clinical settings (Rosenberg et al., N. Engl. J. Med 323:370, 1990; Anderson et al., U.S. Pat. No. 5,399,346).

The vectors described above can additionally comprise sequences encoding one or more selectable markers, including, but not limited to, the gene that encodes dihydrofolate reductase and the genes that confer resistance to neomycin, tetracycline, ampicillin, chloramphenicol, kanamycin and streptomycin resistance.

Delivery of a nucleic acid construct comprising a nucleotide sequence of the present invention under the control of a highly cell-type specific promoter can be by any means known in the art, including oral or intranasal administration; intramuscular, intradermal, intraperitoneal, or subcutaneous injection, including injection using a biological ballistic gun ("gene gun"). Administration of the nucleic acid for therapeutic purposes can be repeated at any desired interval as needed to achieve therapeutic efficacy. Additional components can be added to a vector to improve its selective delivery to target cells and to repress its delivery to non-target cells. Examples of approaches that can be used include host range extension, entry enhancement, and host range restriction, as described in Peng and Russell, Cur. Opin. Biotech. 10: 454-457 (1999), the entirety of which is incorporated herein by reference.

In addition to viral transfer methods, non-viral methods can also be employed to introduce a subject nucleic acid, e.g., an inhibitory nucleic acid molecule according to the invention that corresponds or is complementary to at least a fragment of a p97/VCP nucleic acid molecule that decreases p97/VCP, into the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject nucleic acid by the targeted cell. For example, an inhibitory nucleic acid molecule that targets p97/vasolin containing protein and/or gp78 can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomu-coid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the inhibitory nucleic acid molecules are administered in combination with a liposome and protamine. Other exemplary targeting means of this type include liposomal derived systems, microspheres, polylysine conjugates, and artificial viral envelopes.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Additionally, the non-viral based delivery can be nano-based or aerosolized.

The antisense molecules of the invention can be delivered to cells which express the target nucleic acid in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically. The antisense molecules of the invention can be delivered directly in to the airway, or in an IP formulation, as a nano-based or aerosol drug.

Inhibitory nucleic acid molecule expression for use in polynucleotide therapy methods, for example in particular embodiments, to treat conditions having a IκB/NFκB-mediated chronic inflammatory response, can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers.

More specifically, because it is often difficult to achieve intracellular concentrations of the antisense sufficient to suppress translation on endogenous mRNAs. Therefore, a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous transcripts and thereby prevent translation of the target mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bemoist and Chambon, 1981, Nature 290:304-310.), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue (e.g., for brain, herpesvirus vectors may be used), in which case administration may be accomplished by another route (e.g., systemically).

For any particular subject, the specific dosage regimes should be adjusted over time according to the individual need and the professional judgment of the person administering or supervising the administration of the compositions.

Pharmaceutical Inhibitors

Methods of the invention also feature treatment with pharmaceutical agents, for example, proteasome inhibitors, and additional pharmaceutical agents. Treatment with pharmaceutical agents can be in addition to, e.g. in combination with, other therapies according to the methods of the invention. For example, a method of the invention encompasses treatment with a pharmaceutical agent in addition to an inhibitory nucleic acid molecule.

Suitable pharmaceutical agents include those that inhibit the proteasome, for example inhibit the activity of the proteasome in protein degradation. Included in the scope of the invention are natural and synthetic proteasome inhibitors. Examples of suitable inhibitors include, but are not limited to: MLN-273 and Bortezomib. MLN-273 (Millenium, Inc.) is a small molecule proteasome inhibitor. Bortezomib (Millenium, Inc) Bortezomib (pyrazylcarbonyl-Phe-Leu-boronate) is an extremely potent, stable, reversible and selective inhibitor of chymotryptic threonine protease activity. Bortezomib was first shown to exhibit antitumor properties in a panel of 60 cancer cell lines from the US National Cancer Institute (Adams J. 2004. Cancer Cell. 5:417-421.). Bortezomib is used intravenously to treat multiple myeloma in patients who have received at least one treatment that has not helped. (nlm.nih.gov/medlineplus/drugsinfo). By blocking the proteasome, Bortezomib disrupts numerous biologic pathways, including those related to the growth and survival of cancer cells. Bortezomib selectively induces NFκB mediated apoptosis in cancer cells while normal cells recover from proteasome inhibition (40). Proteasome modulators have recently been shown to be of dual therapeutic importance in pharmaco-gene therapy of cystic fibrosis airway. The proteasome modulating agents LLnL and doxorubicin enhanced CFTR gene delivery and hence CFTR-mediated short circuit current. Moreover these proteasome modulators also inhibited functional ENaC activity and currents independent of CFTR vector administration (41). Other proteasome inhibitors of potential use include ALLN, the bacterial metabolite lactacystin, which is known to inhibit the proteolytic activity of the proteasome. Synthetic analogs have been developed to lactacystin, for example, PS-519. Other natural products reported to inhibit the proteasome include eponemycin and epoxomycin (Sin N, Meng L, Auth H, et al.; 6:1209-1217.) and aclacinomycin A (Figueiredo-Pereira M E, Chen W E, Li J, et al. J Biol. Chem. 1996; 271:16455-16459.).

Additional synthetic proteasome inhibitors include those derived from calpain inhibitor I, and aldehyde inhibitors such as CEP-1612 (An B, Goldfarb R H, Siman R, et al 1998. Cell Death Differ. 5:1062-1075.; Adams J, Behnke M, Chen S, et al. 1998. Bioorg Med Chem. Lett.; 8:333-338.). MG132 is a highly potent reversible inhibitor of the proteasome featuring a high potency (Lee D H, Goldberg A L. Trends Cell Biol. 1998; 8:397-403.). Other proteasome inhibitors include CVT-63417 (Lum R T, Nelson M G, Joly A, et al. 1998. Bioorg Med Chem. Lett. 8:209-214.), PS-341 (61), and the HIV-1 protease inhibitor, ritonavir, which has been shown to be a competitive micromolar inhibitor of the proteasome (André P, Groettrup M, Klenerman P, et al. 1998; Proc Natl Acad Sci USA. 95:13120-13124.).

Additional pharmaceuticals that can be administered in accordance with the invention include, but are not limited to, cystic fibrosis-associated therapies, antibiotic therapy, steroid therapy, anti-asthma therapy, vitamin therapy, sputum-reduction therapy, cystic fibrosis-related diabetes therapy, cystic fibrosis-related liver disease therapy, and oxygen therapy.

Methods of Treatment

The present invention further provides methods of treating a disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a disease or condition having a IκB/NFκB-mediated chronic inflammatory response. The method includes the step of administering to the mammal a therapeutic amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition. The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptibility to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disease or condition having a IκB/NFκB-mediated chronic inflammatory response, or in which a IκB/NFκB-mediated chronic inflammatory response may be implicated.

In one particular aspect, the present invention provides a method of treating an individual having a disorder comprising a IκB/NFκB-mediated chronic inflammatory response component, wherein the method comprises the step of administering to said individual a therapeutically effective amount of an inhibitor of a p97/valosin-containing protein, wherein the inhibition of p97/valosin-containing protein alleviates the IκB/NFκB-mediated chronic inflammatory response component.

In a further particular aspect, the present invention features a method of treating an individual having a disorder comprising a IκB/NFκB-mediated chronic inflammatory response component, wherein the method comprises the step of administering to said individual a therapeutically effective amount of SEQ ID NO. 1 or 2 to reduce or decrease the expression of p97NCP, wherein the decreased expression of p97/valosin-containing protein alleviates the IκB/NFκB-mediated chronic inflammatory response component.

In yet another embodiment, a method provided for treating an individual having a disorder, said disorder comprising a IκB/NFκB-mediated chronic inflammatory response component, comprising the step of administering to said individual a therapeutically effective amount of an inhibitor of a gp78, wherein the inhibition of gp78 alleviates the IκB/NFκB-mediated chronic inflammatory response component.

In still another method of treating an individual having a disorder, said disorder comprising a IκB/NFκB-mediated chronic inflammatory response component, comprising the step of administering to said individual a therapeutically effective amount of a proteasome inhibitor, wherein the inhibition of the proteasome alleviates the IκB/NFκB-mediated chronic inflammatory response component. The proteasome inhibitor can include, but is not limited to, bortezomib or MLN273.

Another particular embodiment of the invention provides a method of treating cystic fibrosis in an individual in need of such treatment, comprising the step of administering one or more inhibitors each of which is capable of reducing cellular degradation of cystic fibrosis transmembrane regulator and IκB, wherein the one or more inhibitors are selected from the group consisting of a p97/valosin-containin protein inhibitor, a gp78 inhibitor, and a proteasome inhibitor.

A still further aspect of the invention provides a method of restoring functional chloride channels in an individual having cystic fibrosis, comprising the step of inhibiting the formation of a complex between p97/valosin-containing protein and a cystic fibrosis transmembrane regulator. The CFTR in this embodiment, and in any other embodiment described herein, can be a mutant or a non-mutant CFTR. Where a mutant CFTR is involved, the inventive methods herein can lead to the restoration of functional chloride channels in a CF cell.

Alternately, in a non-CF cell, the presently disclosed methods can lead to the promotion or enhancement of functional chloride channels in cells.

As described in more detail herein, there is no limitation as to the form, type or nature of the particular inhibitor that is administered to the individual so long as it is capable or effective at achieving the herein described inventive benefits, e.g. alleviation of the IκB/NFκB-mediated chronic inflammatory response component, or restoration of CFTR in the ER and/or cell membrane, or restoration of function chloride ion channels in the cell membrane, or reduction in the cellular degradation of IκB or CFTR by the ERAD pathway and/or the ubiquitin-proteasome pathway, or reduction in the symptoms of the treatable disease, e.g. cystic fibrosis.

In one aspect, the inhibitor can be an inhibitory nucleic acid molecule, such as an shRNA or siRNA, which is effective at inhibiting the expression of p97NCP and/or gp78 such that the interaction between p97NCP and/or gp78 together with CFTR (both mutant and non-mutant forms of CFTR) or with IκB is reduced or inhibited. In a further aspect, the inhibitory nucleic acid molecule, especially an shRNA or siRNA, can be expressed and contained on an expression vector or plasmid, such as, but not limited to a retroviral, adenoviral, adeno-associated viral, or lentiviral vector. The inhibitory nucleic acids can also by any suitable non-viral vector means, such as, by nano-based means, or by microparticle injection (e.g. nucleic acid bombardment techniques), or using any suitable nucleic acid carrier or deliverable matrix. Such inhibitors can be delivered by any suitable means, such as, nasally, and prepared in any deliverable form, such as, for example, intra-peritoneal or aerosolized forms. Further description of the inhibitory nucleic acids of the invention are described herein elsewhere.

In another aspect, the inhibitor can be a small molecule inhibitor which is effective at inhibiting the interaction between p97/VCP and/or gp78 together with CFTR (both mutant and non-mutant forms of CFTR) or with IκB is reduced or inhibited. As used herein, a small molecule inhibitor can refer to a compound that decreases, suppresses, attenuates, diminishes, arrests, or stabilizes the activity of a molecule. A small molecule inhibitor can also refer to a compound that interacts or binds to a target protein of the invention, e.g. p97/VCP and/or gp78 and/or a proteasome component, such that the function of the target protein is reduced, decreased, suppressed, attenuated, diminished, arrested and in particular, wherein the function includes facilitating the degradation of certain proteins of the invention, e.g. CFTR or IκB, via the ERAD pathway and/or the ubiquitin-proteasome pathway. Examples of small molecule inhibitors can include, but are not limited to, chemical chaperones, molecular chaperones, or natural compounds, e.g. glycerol, DMSO, overexpression of a VCP binding partner such as gp78.

In still another aspect, the inhibitor can be a functional inhibitor, defined herein elsewhere, which is effective at inhibiting the interaction between p97/VCP and/or gp78 together with CFTR (both mutant and non-mutant forms of CFTR) or with IκB. For example, a functional inhibitor can include an ATPase inhibitor (e.g. hemin) or any compound that lowers ATP levels, tyrosine kinase activity inhibitor, genistein, or a protein tyrosine phosphatase inhibitor.

In one aspect, the disorder and/or disease treatable by the present inventive methods is cystic fibrosis. In another aspect, the disorder and/or disease bears a IκB/NFκB-mediated chronic inflammatory response component and can include diseases, such as, but not limited to, forms of diabetes insipidus, type II diabetes, Parkinson's Disease, Alzheimer's Disease, amyloidosis, surfactant protein C deficiency, ABCA3 deficiency, Huntington's Disease, adrenoleukodystrophy, amyotrophic lateral sclerosis, retinitis pigmentosa, polyglutamine diseases, mad cow disease, alpha one antitrypsin deficiency, short chain acyl CoA dehydrogenase deficiencies inclusion body myositis aging, chronic inflammatory diseases, chronic obstructive pulomonary disorder, chronic bronchitis, chronic sinusitis, chronic inflammatory conditions, inflammatory bowel diseases, including ulcerative colitis and crohn's disease. In a particular embodiment, the disorder is cystic fibrosis caused by a deletion of phenylalanine at position 508 of the cystic fibrosis transmembrane regulator. However, the inventive methods described herein are limited to any particular cystic fibrosis mutation and can include the treatment of any form of cystic fibrosis caused by any known mutation, and in particular, any mutation in CTFR.

The herein described methods can also include the coadministration of a cystic fibrosis-associated therapy that may further benefit in an additive or synergistic manner the treatment of the disorder. Such additional or supplemental therapies can include any suitable and/or standard cystic fibrosis therapy, such as, including a antibiotic therapy, a steroid therapy, an anti-asthma therapy, a vitamin therapy, a sputum-reduction therapy, a cystic fibrosis-related diabetes therapy, a cystic fibrosis-related liver disease therapy, an oxygen therapy, and any form of physical therapy useful in removal of CF sputum and mucosal respiratory discharge.

Pharmaceutical Compositions and Therapeutic Uses

Pharmaceutical compositions can comprise inhibitory polynucleotides and/or pharmaceutical agents of the claimed invention. The pharmaceutical compositions will comprise a therapeutically effective amount of either polynucleotides and/or pharmaceutical agents of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician.

In the invention, a therapeutically effective amount of an inhibitor can be the amount that is effective to establish a concentration of the inhibitor in body fluids at about 1 nm to about 10 mM in the individual. For purposes of the present invention, an effective dose of siRNA/inhibitor will be from about 0.01 mg/kg to 100 mg/kg, of the inhibitory nucleic acid constructs in the individual to which it is administered. For purposes of the present invention, an effective dose virus mediated gene therapy will be from about 1 to 1000 ul volume for 0.1 to $5 \times 10^{11}$ viral particles in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991). Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

Once formulated, the nucleic acid compositions of the invention can be (1) administered directly to the subject; (2) delivered ex vivo, to cells derived from the subject or (3) delivered in vitro for expression of recombinant proteins. Methods for the ex vivo delivery and reimplantation of transformed cells into a subject are known in the art and described in e.g., International Publication No. WO 93/14778. Examples of cells useful in ex vivo applications include, for example, stem cells, particularly hematopoetic, lymph cells, macrophages, dendritic cells, or tumor cells.

Both the dose of the antisense composition and the means of administration are determined based on the specific qualities of the therapeutic composition, the condition, age, and weight of the patient, the progression of the disease, and other relevant factors. Administration of the therapeutic antisense agents of the invention includes local or systemic administration, including injection, oral administration, particle gun or catheterized administration, and topical administration. Preferably, the therapeutic antisense composition contains an expression construct comprising a promoter and a polynucleotide segment of at least about 12, 22, 25, 30, or contiguous nucleotides of the antisense strand of a nucleic acid. Within the expression construct, the polynucleotide segment is located downstream from the promoter, and transcription of the polynucleotide segment initiates at the promoter.

Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art. The therapeutic nucleic acids of the present invention may be utilized in gene delivery vehicles. The gene delivery vehicle may be of viral or non-viral origin (see generally, Jolly, Cancer Gene Therapy (1994) 1:51-64; Kimura, Human Gene Therapy (1994) 5:845-852; Connelly, Human Gene Therapy (1995) 1:185-193; and Kaplitt, Nature Genetics (1994) 6:148-153). Gene therapy vehicles for delivery of constructs including a coding sequence of a therapeutic of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

Delivery of the shRNA plasmid can be viral mediated, for example lentiviral/retroviral/adenoviral The present invention can employ recombinant retroviruses which are constructed to carry or express a selected nucleic acid molecule of interest. Retrovirus vectors that can be employed include those described in EP 0415 731; WO 90/07936; WO 94/03622; WO 93/25698; WO 93/25234; U.S. Pat. No. 5,219,740; WO 93/11230; WO 93/10218; Vile and Hart, Cancer Res. (1993) 53:3860-3864; Vile and Hart, Cancer Res. (1993) 53:962-967; Ram et al., Cancer Res. (1993) 53:83-88; Takamiya et el., J. Neurosci. Res. (1992) 33:493-503; Baba et al., J. Neurosurg. (1993) 79:729-735; U.S. Pat. No. 4,777,127; GB Patent No. 2,200,651; and EP 0 345 242.

Gene delivery vehicles of the present invention can also employ parvovirus such as adeno-associated virus (AAV) vectors. Representative examples include the AAV vectors disclosed by Srivastava in WO 93/09239, Samulski et al., J. Vir. (1989) 63:3822-3828; Mendelson et al., Virol. (1988) 166:154-165; and Flotte et al., PNAS (1993) 90:10613-10617. Representative examples of adenoviral vectors include those described by Berkner, Biotechniques (1988) 6:616-627; Rosenfeld et al., Science (1991) 252:431-434; WO 93/19191; Kolls et al., PNAS (1994) 91:215-219; Kass-Eisler et al., PNAS (1993) 90:11498-11502; Guzman et al., Circulation (1993) 88:2838-2848; Guzman et at, Cir. Res. (1993) 73:1202-1207; Zabner et al., Cell (1993) 75:207-216; Li Ct et al., Hum. Gene Ther. (1993) 4:403-409; Cailaud et al., Eur. J. Neurosci. (1993) 5:1287-1291; Vincent et al., Nat. Genet. (1993) 5:130-134; Jaffe et al., Nat. Genet. (1992) 1:372-378; and Levrero et al., Gene (1991) 101:195-202. Exemplary adenoviral gene therapy vectors may also include those described in WO 94/12649, WO 93/03769; WO 93/19191; WO 94/28938; WO 95/11984 and WO 95/00655. Administration of DNA linked to killed adenovirus as described in Curiel, Hum. Gene Ther. (1992) 3:147-154 may be employed.

Other gene delivery vehicles and methods may be employed, including polycationic condensed DNA linked or unlinked to killed adenovirus alone, for example Curia Hum. Gene Ther. (1992)3.147-154; ligand linked DNA, for example see Wu, J. Biol. Chem. (1989) 264:16985-16987;

eukaryotic cell delivery vehicles cells, for example see U.S. Ser. No. 08/240,030, filed May 9, 1994, and U.S. Ser. No. 08/404,796; deposition of photopolymerized hydrogel materials; hand-held gene transfer particle gun, as described in U.S. Pat. No. 5,149,655; ionizing radiation as described in U.S. Pat. No. 5,206,152 and in WO92111033; nucleic charge neutralization or fusion with cell membranes.

Naked DNA may also be employed. Exemplary naked DNA introduction methods are described in WO 90111092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Nos. WO 95/13796, WO 94/23697, and WO 91/14445, and EP No. 0524 968.

Further non-viral delivery suitable for use includes mechanical delivery systems such as the approach described in Woffendin et al., Proc. Natl. Acad. Sci. USA (1994) 91(24): 11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033. Nano-based delivery means may be used as well.

Administration of the pharmaceutical compositions of the invention can be by any suitable means, such as, for example oral administration, parenteral administration, transdermal administration, nasal administration, aerosol administration, topical administration or by direct injection. Administration of the pharmaceutical compositions of the invention can also be carried at or substantially at the same time as the administration of one or more additional proteasome inhibitors. Administration of the pharmaceutical compositions of the invention can also be carried at or substantially at the same time as the administration of one or more cystic fibrosis-associated therapies, antibiotic therapy, a steroid therapy, an anti-asthma therapy, a vitamin therapy, a sputum-reduction therapy, a cystic fibrosis-related diabetes therapy, a cystic fibrosis-related liver disease therapy, and an oxygen therapy. The pharmaceutical compositions of the invention and the one or more additional proteasome inhibitors, or one or more cystic-fibrosis associated therapies, can be formulated as a single pharmaceutical composition or prepared as separate compositions. The amount of active ingredient that can be combined with a carrier material to produce a single dosage form will generally be that amount of the compound that is therapeutically effective as described herein. Generally, out of one hundred percent, this amount will range from about 1 percent to about ninety-nine percent of active ingredient, preferably from about 5 percent to about 70 percent, most preferably from about 10 percent to about 30 percent.

Pharmaceutical compositions for oral administration can be formulated using pharmaceutically acceptable carriers well known in the art in dosages suitable for oral administration and which are in such an amount or dosage which is sufficient to detect a therapeutic effect. A therapeutic effect can be detected by, for example, chemical markers or antigen levels. Therapeutic effects also include reduction in physical symptoms, such as decreased body temperature. Such carriers enable the pharmaceutical compositions to be formulated as tablets, pills, dragees, capsules, caplets, liquids, gels, gel caps, syrups, slurries, suspensions and the like, for ingestion by the subject.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage. Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may, be dissolved or suspended in suitable liquids, such as fatty oils, liquid paraffin, or liquid polyethylene glycol with or without stabilizers.

Compounds of the invention can be delivered directly to selected sites in the body by a variety of means, including injection, infusion, catheterization and topical application, among others. Compounds of the invention also may be bound to carrier bio-compatible particles, e.g., autologous, allogenic or xenogenic cells, to facilitate targeted delivery of the substance. Unless otherwise specified, the discussion set forth below refers to binding of compounds of the invention to cells, either by direct delivery to the disease site, or in the preparation of carrier vehicles.

In exemplary embodiments, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions. Injection of the compositions of the invention can be carried out by directly injecting the compositions into or substantially nearby a tumor or solid cancer.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

For nasal administration, penetrants appropriate to the particular bather to be permeated can be used in the formulation. Such penetrants are generally known in the art. The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the compounds of the invention from subcutaneous or intramuscular injection. This may be accomplished by the use of a liquid suspension of crystalline or amorphous material having poor water solubility. The rate of absorption of the compounds then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

After pharmaceutical compositions comprising a compound of the invention formulated in an acceptable carrier have been prepared, they can be placed in an appropriate container and labeled for use in accordance with the methods described herein along with information including amount, frequency and method of administration.

The pharmaceutical composition may be formulated from a range of preferred doses, as necessitated by the condition of the patient being treated. For example, the imaging compounds described herein may preferably be 60%, 61%, 62%, 63%, 64%, 65%, 70%, 75%, 80%, 85%, 86%, 87%, 88%, 89%, 90%, and any percentage between 60% and 90%, of the weight of the composition.

In embodiments involving the co-administration of another active ingredient, such as, for example, a proteasome inhibitor, or a pharmaceutical agent that inhibits the proteasome, or a cystic fibrosis-associated therapy such as an antibiotic therapy, a steroid therapy, an anti-asthma therapy, a vitamin therapy, a sputum-reduction therapy, a cystic fibrosis-related diabetes therapy, a cystic fibrosis-related liver disease therapy, and an oxygen therapy. The inhibitory nucleic acids of the invention can be administered in combination therewith in a ratio in the range of 1:1-1:5, 1:1-1:10, 1:1-1:25, 1:1-1:50. 1:1-1:100, 1:1-1:500, 1:1-1:1000, 1:1-1:10,000, 5:1-1:1, 10:1-1:1, 25:1-1-1, 50:1-1:1, 100:1-1:1, 500:1-1:1, 1000:1-1:1 or 10,000:1-1:1.

Preferably, a detectably effective amount of the inhibitory agent, for example the inhibitory nucleic acid, of the invention is administered to a subject. In accordance with the invention, an "effective amount" is meant the amount of an agent required to ameliorate the symptoms of a disease relative to an untreated patient. The effective amount of active agent(s) used to practice the present invention for therapeutic treatment of a cystic fibrosis varies depending upon the manner of administration, the age, body weight, and general health of the subject. Ultimately, the attending physician or veterinarian will decide the appropriate amount and dosage regimen. "A detectably effective amount of the inhibitory agent of the invention may be administered in more than one injection. The detectably effective amount can vary according to factors such as the degree of susceptibility of the individual, the age, sex, and weight of the individual, idiosyncratic responses of the individual, the dosimetry. Optimization of such factors is well within the level of skill in the art. Moreover, two or more agents of the invention can be co-administered in any suitable ratio and in combination with other active ingredients that can be co-administered therewith, such as, other proteasome The amount of an agent used in accordance with the methods disclosed herein will depend upon the body mass of the patient, the nature and severity of the condition being treated, the nature of therapeutic treatments which the patient has undergone, and on the idiosyncratic responses of the patient, and the state or status of the disease or condition being treated. Ultimately, the attending physician or veterinarian will decide the appropriate amount and dosage regimen.

Kits and/or Pharmaceutical Packages

The invention provides kits or pharmaceutical packages for the treatment of a disease or condition as described herein, such as a cystic fibrosis. In one embodiment, the kit comprises a therapeutically effective dose of an inhibitor of gp78 to treat any of the diseases or conditions as specified by the invention, and instructions for use thereof. The kits provided by the invention can further comprise a therapeutically effective dose of one or both of an inhibitor of p97/valosin-containing protein or a proteasome inhibitor. The proteasome inhibitor can be any of the proteasome inhibitors listed herein, including, but not limited to MLN-273, bortezomib, LLnL, doxorubicin, ALLN, lactacystin, PS-519, eponemycin, epoxomycin, aclacinomycin A (59), synthetic proteasome inhibitors include those derived from calpain inhibitor I, and aldehyde inhibitors such as CEP-1612 (60, 61), MG132, CVT-63417 (63), PS-341 (61), and the HIV-1 protease inhibitor, ritonavir.

In preferred aspects of the invention, the kits comprise an inhibitor that is an inhibitory nucleic acid molecule selected from the group consisting of an inhibitory nucleic acid molecule is an inhibitory nucleic acid molecule that corresponds or is complementary to at least a fragment of a nucleic acid molecule encoding the gp78.

The kits can also comprise, together or separate from the inhibitory agents of the invention, additional active ingredients useful inhibiting the proteasome. For example, such additional active ingredients can include any known agent that inhibits proteasome activity. The kits can also comprise a cystic fibrosis-associated therapy selected from the group consisting of an antibiotic therapy, a steroid therapy, an anti-asthma therapy, a vitamin therapy, a sputum-reduction therapy, a cystic fibrosis-related diabetes therapy, a cystic fibrosis-related liver disease therapy, and an oxygen therapy.

Optionally, the kits include directions for the treatment of a disease or condition in a subject with the compositions of the invention. The kits can also include the pharmaceutical compositions of the invention described herein and can include instructions and any devices which are necessary or advantageous or useful for the administration of the pharmaceutical compositions or inventive compounds, e.g. a syringe or delivery implement. The container is not intended to be limited to any particular form, shape, or size and its construction can be of any suitable material in the art that is not detrimental to the contents contained therein. For example, the kit can comprise a sterile container which contains the inhibitory agent of the invention, and other necessary reagents; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the inhibitory agents described herein and their use in treating the diseases or conditions described herein. In other embodiments, the instructions include at least one of the following: description of the inhibitory nucleic acids; methods for using the enclosed materials for the treatment of the indicated disease or condition; precautions; warnings; indications; clinical or research studies; and/or references. The instructions may be printed directly on the container (when present), or as a label applied to the container, or as a separate sheet, pamphlet, card, or folder supplied in or with the container.

All the essential materials and reagents required for administering the compounds of the invention can be assembled together in the herewith kits. When the components of the kit are provided in one or more liquid solutions, the liquid solution preferably is an aqueous solution, with a sterile aqueous solution being particularly preferred.

The components of these kits may be provided in dried or lyophilized forms. When reagents or components are provided in dried form, reconstitution generally is by the addition of a suitable solvent. It is envisioned that the solvent also may be provided in another container means. The kits of the invention may also include an instruction sheet defining administration of the compounds of the invention or for explaining the desired procedures contemplated by the present invention, such as, for example, in the treatment of a disease or condition described herein, for example cystic fibrosis.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle. Other instrumentation includes devices that permit the reading or monitoring of reactions in vitro.

This invention is further illustrated by the following examples, which should not be construed as limiting. All documents mentioned herein are incorporated herein by reference.

EXAMPLES

The invention will now be further described by way of the following non-limiting examples. Considered first are the materials and methods which were used in the examples.
Materials and Methods of the Invention
The results reported herein were obtained using the following Materials and Methods:

Human Subjects.

Cystic Fibrosis (CF) (homozygous ΔF508) and non-CF subjects (n=3, ages 7 through 9 years) who were undergoing fiberoptic bronchoscopy and bronchoalveolar lavage for a clinical indication were invited to participate in a Johns Hopkins Institutional Review Board (JHIRB) and GCRC-approved protocol. Parents signed informed consent on behalf of their children. Bronchial brushings were obtained after bronchoalveolar lavage to minimize contamination with mucous and neutrophils. Brushes were directly immersed in cell culture medium on ice for later transport to the laboratory.

Investigational Therapeutics.

The proteasome inhibitors, Bortezomib (Johns Hopkins Pharmacy) and MLN-273 (under a material transfer agreement) were obtained from Millenium Pharmaceuticals Inc., Cambridge, Mass. 4-phenylbutyrate (4-PBA) was obtained from Sigma, St. Louis, Mo.

Antibodies and Plasmids.

The anti-CFTR (169) and anti-gp78 rabbit polyclonal antibodies have been previously described (8,10). Mouse/rabbit polyclonal anti-VCP antibodies were obtained from Affinity Bioreagents (ABR), Golden, Colo. and Santa Cruz Biotechnology, Inc., Santa Cruz, Calif. Anti-Hsp90 (rat monoclonal), Hsp70 (mouse monoclonal/rabbit polyclonal), Hsc70 (rabbit polyclonal) and Hsp40 (rabbit polyclonal) antibodies were purchased from Stressgen Biotech. Inc., San Diego, Calif. The anti-CHIP rabbit polyclonal was obtained from Abcam Inc., Cambridge, Mass. The plasmid constructs pCIneo-gp78, pCIneo-gp78C and VCPQQ have been previously described (8). The ΔF508-CFTR and wt-CFTR-GFP were constructed in the pS65T-C1 vector. VCP shRNA was constructed in the pSM2 vector (Open Biosystems, Huntsville, Ala.).

Protocol for Construction of VCPshRNA.

Oligo design and polymerase chain reaction (PCR): The single oligo containing the hairpin and common 5' and 3' ends, was used as a PCR template. The oligo was PCR amplified using universal primers which contain XhoI (5' prime) and EcoRI (3' prime). These PCR fragment was then cloned into the hairpin cloning site of pSHAG-MAGIC2/pSM2 (Open Biosystems). VCPanti-sense/target sequence 22mer is shown in bold and common mir30 contexts regions are underlined. The VCP shRNA was amplified using Advantage-GC PCR kit (Qiagen) using single strand 97 nt "mir30-like" DNA template oligo (TGCTGTTGACAGTGAGCGCCCGCAA-GAAGATGGATCTCATTAGTGAAGCCACAGA TGTAATGAGATCCATCTTCTTGCGGAT-GCCTACTGCCTCGGA) and 5' miR30PCRxhoIF (CA-GAAGGCTCGAGAAGGTATATTGCTGT-TGACAGTGAGCG) and 3' miR30PCREcoRIF (CTAAAGTAGCCCCTTGAATTCCGAG-GCAGTAGGCA) primers. PCR conditions were (94° C. 30s, 94° C. 30s & 55° C. 30s 25 cycles, 75° C. 10 min, 4° C. forever)

Cloning.

The 100 uL PCR reaction was purified by phenol: chloroform extraction, and then following a single chloroform extraction, the pellet was resuspended in 10 mM Tris and digested with EcoRI & XhoI. Fragment was gel purified using QiaxII gel purification kit (Qiagen) and resuspended in 10 uL of 10 mM Tris, pH 7-8. The pSM2 vector (2 ug) was similarly cut by EcoRI & XhoI, gel purified, and resuspended in 10 uL of 10 mM Tris, pH 7-8. The EcoRI-XhoI cut PCR product (5 ul) and vector (1 ul) were ligated using Rapid DNA ligation kit (Roche) in a 20 uL ligation reaction. Briefly, the single oligo containing the hairpin and common 5' and 3' ends, was used as a PCR template. The oligo was PCR amplified using universal primers which contain XhoI (5' prime) and EcoRI (3' prime). These PCR fragment was then cloned into the hairpin cloning site of pSM2. VCPanti-sense/target sequence 22mer is shown in bold and common mir30 contexts regions are shown in italics. The sequences of the VCP shRNA are shown in FIG. 8, and below:

| SEQ ID NO: 1 | CCCGCAAGAAGATGGATCTCAT |
|---|---|
| SEQ ID NO: 2 | ATGAGATCCATCTTCTTGCGGA |

The VCP shRNA was amplified using Advantage-GC PCR kit (Qiagen) using single strand 97 nt "mir30-like" DNA template oligo (TGCTGTTGACAGTGAGCGCCCGCAA-GAAGATGGATCTCATTAGTGAAGCCACAGATG TAATGAGATCCATCTTCTTGCGGATGC-CTACTGCCTCGGA) and 5' miR30PCRxhoIF (CAGAAG-GCTCGAGAAGGTATATTGCTGTTGACAGTGAGCG) and 3' miR30PCREcoRIF (CTAAAGTAGCCCCTTGAAT-TCCGAGGCAGTAGGCA) primers. PCR conditions were (94° C. 30 s, 94° C. 30 s & 55° C. 30 s 25 cycles, 75° C. 10 min, 4° C. forever). CHOP shRNA was purchased from (Open Biosystems, Huntsville, Ala.).

Cell Culture, Transfection and Metabolic Labeling.

The IB3-1 (ΔF508/W1282X; low level expression of ΔF508-CFTR and no W1282X protein), CFTE (ΔF508-homozygous) and S9 (IB3-1 corrected by AAV-CFTR) cells were maintained in LHC-8 media containing 100 units/ml penicillin, 100 μg/ml streptomycin, 0.25 μg/ml amphotericin B and 10% fetal bovine serum. LHC-8 media was purchased from Biosource and other components were purchased from Gibco (Invitrogen, Carlsbad, Calif.). The cells were plated on 6-well plates and transfected with 4 μg plasmid DNA each of ΔF508/wt-CFTR-GFP and co-transfected with VCP shRNA (ΔVCP), VCPQQ construct (deficient in two AAA ATPase domains, D1 & D2), gp78 siRNA (Δgp78) or gp78ΔC (deficient in VCP binding domain) constructs using Lipofectamine 2000 (Invitrogen, Carlsbad, Calif.) as described by the manufacturer. After 48 hrs of transfection, cells were rinsed three times and starved for 1 hr in methionine- and cysteine-free Dulbecco's modified Eagle's medium (DMEM). Cells were pulse labeled with 250 μci/ml [$^{35}$S]-methionine and cysteine (ICN Biomedical, Irvine, Calif.) for 30 min and than chased in DMEM containing 10 mM methionine and 4 mM cysteine for indicated times.

Fluorescence Microscopy.

After 48 hrs of transfection, cells were washed three times with Hank's balanced salt solution containing calcium and magnesium (Invitrogen, Carlsbad, Calif.), and loaded with 1 μM ER-Tracke™ Blue-White DPX dye (Molecular Probes, Invitrogen, Carlsbad, Calif.). Plates were incubated at 37° C., 5% $CO_2$ for 2 hours and examined under the Zeis Axiovert 135-N fluorescent microscope. The Quantix 1401 CCD camera and the IP Lab software v. 3.5 with appropriate filter settings for GFP (FITC) or ER-Tracker Blue (DAPI) were used to capture the images.

Immunoprecipitation and Immunoblotting.

Cells were lysed directly on plates using M-PER (Pierce Biotech. Inc., Rockford, Ill.) protein lysis buffer containing protease inhibitor cocktail (Roche) after three washes with ice cold PBS. CF bronchial brushings were transferred to lysis buffer. For immunoprecipitation, 500 μg/ml (cell culture)/50 μg/ml (bronchial brushings) total protein extracts were incubated with 50 μl of protein A/G agarose beads (Santa Cruz Biotechnology Inc., Santa Cruz, Calif.) for 3 hours at 4° C. After preclearing, 5 μg of respective primary antibody or pre-immune sera (negative control) was added to each tube. After 1 hour, protein A/G agarose beads (50 μL) were added to each tube and tubes were incubated overnight at 4° C. Beads were washed once with lysis buffer (20 mM Tris-HCl [pH 7.6], 150 mM NaCl, 0.5% Triton X-100 and 10 μM phenylmethylsulfonyl fluoride [PMSF]) followed with two washes with phosphate buffer saline (PBS). The beads were suspended in Laemmli's sample buffer (30 μL) containing β-mercaptoethanol, vortexed for 1 minute, resolved by 4-10% SDS-PAGE and transferred to a 0.4-μm pore size nitrocellulose membrane. Proteins were detected using respective primary antibodies. For pulse chase experiments, CFTR immunoprecipitate was eluted with sample buffer and separated on a 4-8% SDS-PAGE, dried for 2 hours and processed for autoradiography.

IL8 Cytokine ELISA.

The IB3-1 cells were transfected with ΔVCP, VCPQQ, Δgp78 and gp78ΔC constructs, and treated with 5 μM bortezomib or 5 mM 4-phenylbutyrate (4PBA). IB3-1 cells were induced with 1 ng/ml IL-1β, 24 hr post-transfection. After 48 hrs of transfection, supernatants were collected and IL-8 levels were measured using solid-phase amplified sensitivity immunoassay (EASIA) as specified by the manufacturer (BioSource International, Inc., Camarillo, Calif.). Standards, and high and low cytokine controls were included. The plates were read at 450 nm on 96-well microplate reader (Molecular Devices) using SOFT-MAX-Pro software. The mean blank reading was subtracted from each sample and control reading. The amount of substrate turnover was determined calorimetrically by measuring the absorbance which is proportional to IL8 concentration. A standard curve was plotted and an IL8 concentration in each sample was determined by interpolation from standard curve. The data represents mean of three independent experiments±SD.

NoShift NFκB Binding Assay.

IB3-1 cells transfected (24 hrs) with ΔVCP, ΔF508 or ΔCHOP were treated with 5 μM bortezomib (6 hrs)/5 μM MLN-273 (6 hrs)/5 mM 4PBA (24 hrs). Cells were induced with IL-β(1 ng/ml) for 12 hrs. After 24 hrs of transfection, nuclear extracts (11) were collected using NucBuster protein extraction kit (Novagen, San Diego, Calif.) and the shift in bound NFκB was measured using NoShift NFκB Binding Assay kit (Novagen, San Diego, Calif.) as specified by the manufacturer. The signal from nuclear extracts was compared with the negative control (minus extract). The specificity of protein binding was established using NFκB specific and mutant competitors. The plates were read at 450 nm on 96-well microplate reader (Molecular Devices) using SOFT-MAX-Pro software. The absorbance readings were used to determine the levels of bound NFκB. The data represents mean of three independent experiments±SD.

MQAE Assay.

CFTR-mediated chloride transport activity in IB3-1 cells transfected with ΔVCP, VCPQQ, Δgp78 and gp78ΔC constructs, and treated with bortezomib (1, 5 or 10 µM) was assayed by the halide-sensitive dye, MQAE. Fluorescence of MQAE is quenched by halides. Cells were grown on glass coverslips in DMEM containing 10% FBS. Cells were loaded with the dye by hypotonic shock at 37° C. for 40 min in Opti-MEM/water (1:1) containing 10 mM MQAE, washed and then mounted in a perfusion chamber for fluorescence measurements. Fluorescence was measured using a Zeiss inverted microscope coupled to a CCD camera Excitation and emission wavelengths were 350 nm and 460 nm, respectively. The stage and objective lenses were maintained at 37° C. The media was kept flowing through the perfusion chamber at 1 ml/min using a peristaltic pump. Both 10 µM forskolin and 10 µM genistein were used to induce Cl⁻ transport in IB3-1 cells. CFTR was inhibited with either 5 µM CFTR inhibitor 172 (12) or 14-22 amide (Calbiochem, San Diego, Calif.) to reduced cAMP mediated phosphorylation. Chloride efflux was calculated using following equations:

$$F0/FCl = 1 + [Cl-]i * Ksv \quad (1)$$

$$F0 = F20 * (1 + 0.02 * Ksv) \quad (2)$$

$$(dCl/dt) = F0/[Ksv*(FCl)2]*dFCl/dt \quad (3)$$

Statistical Analysis.

All data are represented as the mean±SD of three experiments. The one-way ANOVA with a Dunnett planned comparison was run for each sample versus control. A *$P<0.05$ was considered to have statistical significance.

Example 1

Valosin Containing Protein/p97 Participates in Endoplasmic Reticulum Associated Degradation of ΔF508-Cystic Fibrosis Transmembrane Receptor Previously, using a combination of bioinformatics tools for iterative database searches and multiple sequence alignment, we found that most of the 2-domain AAA⁺ proteins like VCP (valosin containing protein)/p97 and CFTR (cystic fibrosis transmembrane regulator) are associated with membrane function while 1-domain AAA⁺ proteins largely include regulatory subunits of 26S protease (PSMC 1, 2, 3, 4 and 6). The most common mutation in cystic fibrosis (ΔF508-CFTR; (deletion in phenylalanine at position 508 of the CFTR)) is located in first AAA⁺ domain (amino acid 508), resulting in misfolding and subsequent degradation of CFTR.

To test the hypothesis that valosin containing protein (VCP) is involved in ΔF508 cystic fibrosis transmembrane receptor (CFTR) degradation, VCP protein levels were measured in freshly isolated bronchial epithelial cells from ΔF508 cystic fibrosis (CF) and non-cystic fibrosis (non-CF) subjects. VCP levels were upregulated in all ΔF508 CF subjects as compared to non-CF controls (FIG. 1A). Moreover, the difference between CF and non-CF bronchial expression was striking. Next, transient knock down of either VCP or gp78 was performed to examine if knockdown of either protein would rescue ΔF508-CFTR from endoplasmic reticulum associated degradation (ERAD) in cystic fibrosis bronchial epithelial cells. To reduce the expression of these proteins, short hairpin/si RNA was used. The efficiency of VCP short hairpin RNA (ΔVCP) mediated inhibition of VCP protein levels in IB3-1 cells (cystic fibrosis bronchial epithelial line ΔF508/W1282X) (13) was evaluated by immunoblotting of whole cell lysates, as shown in FIG. 1B, upper panel. To enhance the ΔF508-CFTR signal, the IB3-1 cells were transfected with ΔF508-CY1R-GFP, and co-transfected with ΔVCP or a plasmid control. Inhibition of VCP was associated with the accumulation of ΔF508-CFTR-GFP in the endoplasmic reticulum (ER), as compared to control, shown in the lower panel of FIG. 1B. The accumulation of ΔF508-CFTR in ER was confirmed by co-localization of GFP signal with the signal from ER Tracker Blue-White DPX dye. Furthermore, spreading of the GFP signal beyond the ER tracker dye compartment suggested that the ΔF508-CFTR-GFP escaped from ER in ΔVCP IB3-1 cells (FIG. 1C). Together, these data demonstrate that valosin containing protein/p97 participates in Endoplasmic reticulum associated degradation of ΔF508-cystic fibrosis transmembrane receptor.

Example 2

VCP/p97 Inhibition Rescues ΔF508-Cystic Fibrosis Transmembrane Receptor from Endoplasmic Reticulum Associated Degradation In IB3-1 the endomplasmic reticulum (ER)-retained ΔF508-cystic fibrosis transmembrane receptor (CFTR) protein is core-glycosylated (160 KD immature/B form), whereas growth at 26° C. allows ΔF508-CFTR protein to transit the biosynthetic pathway and acquire complex glycosylation (180 kD mature/C form) (5). Moreover, ΔF508 band C form has a faster turnover rate from the plasma membrane (14). To assess the effects of ΔVCP on the stability of ΔF508-CFTR bands B and C, IB3-1 cells were first transiently transfected with ΔF508-CFTR-GFP for 48 hrs, and then metabolically labeled with ³⁵S-methionine. ΔF508-CFTR was immunoprecipitated with anti-CFTR 169 antibody (15) after the indicated chase time, as shown in FIG. 2A. Co-transfection with ΔVCP (FIG. 2A) resulted in stabilization of both immature B and mature C forms. By comparison, co-transfection with gp78siRNA (Δgp78) produced only a transient rescue of mature C form with peak at 1 hr (FIG. 2A), suggesting that VCP, not gp78, is central to extraction of CFTR from endoplasmic reticulum (ER) for endoplasmic reticulum associated degradation (BRAD). S9 cells (IB3-1 cells that are corrected with wildtype CFTR) were similarly transfected with additional wt-CFTR and ΔVCP. There was an efficient maturation and stability of band B to band C (FIG. 2B), confirming that wt- and ΔF508-CFTR are extracted and degraded through the same VCP-mediated pathway.

Figure 2B:
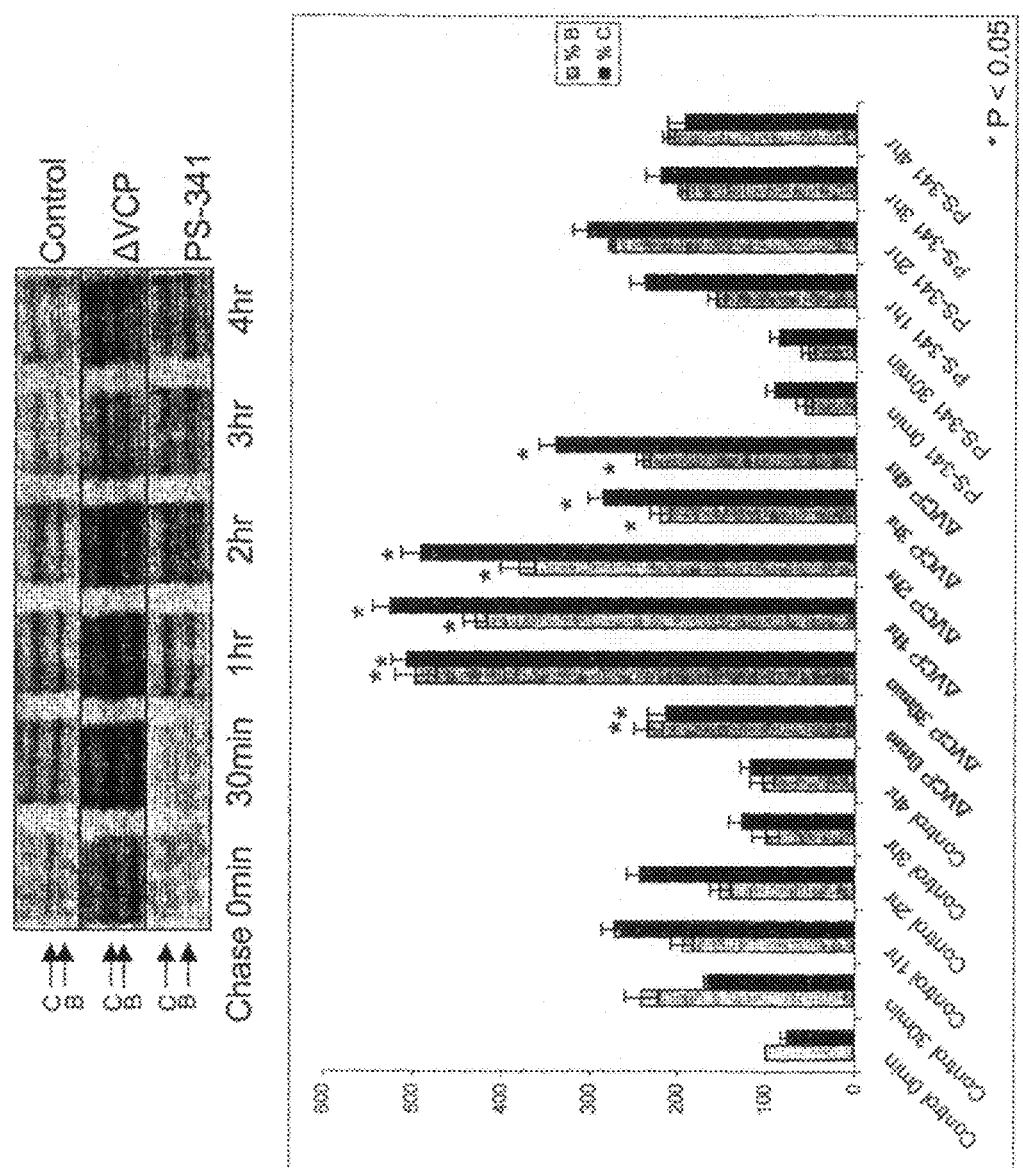
Figure 2C:
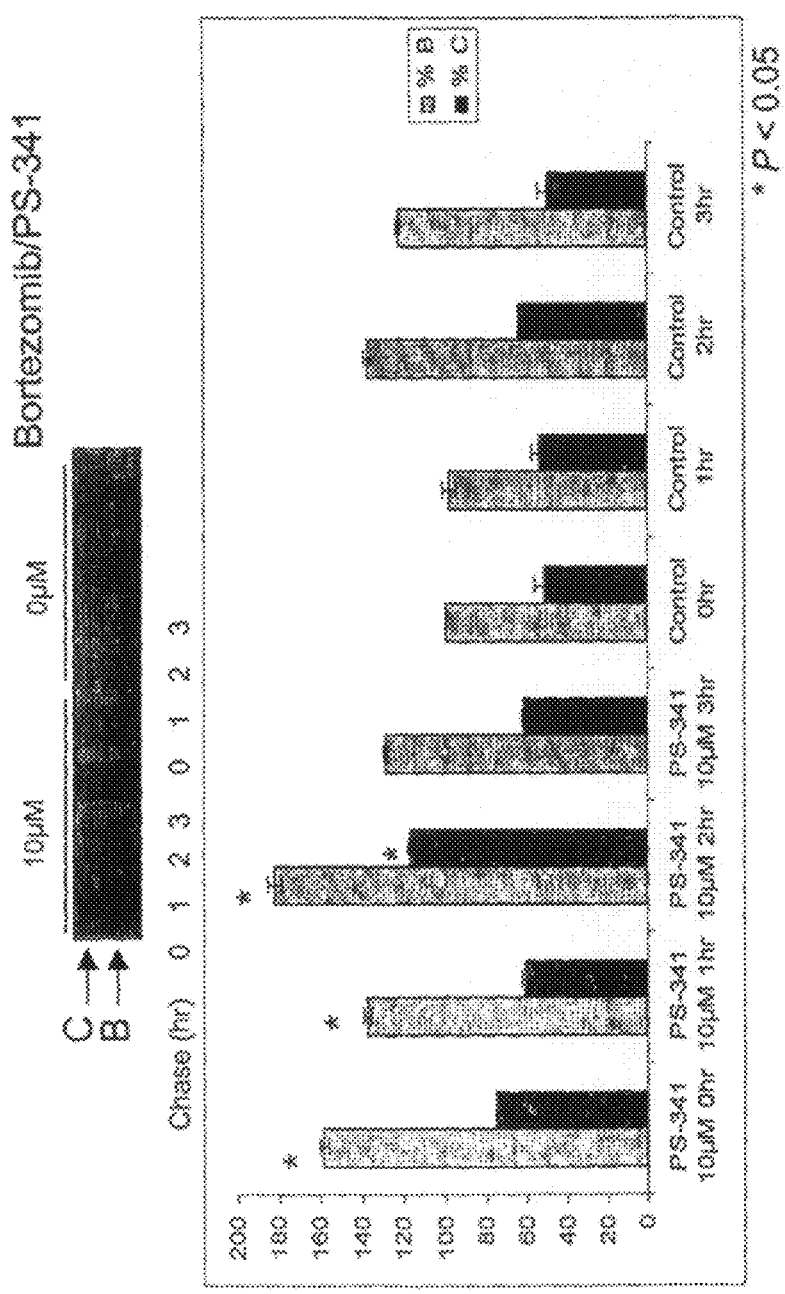

The proteasomal compartment is a potential therapeutic target for cystic fibrosis, not only because of the potential role of VCP in proteasome-mediated degradation of CFTR, but also because both VCP and proteasome inhibitors are known to stabilize IκB, the inhibitor of the NFκB mediated inflammatory response (16,17). Bortezomib (6 hrs treatment) was used at a 10-µM dose, which led to partial inhibition of protease activity in IB3-1 cells. Phase microscopic examination revealed no difference in morphology of treated and untreated monolayers (data not shown). To study the effect of bortezomib on another epithelial cell type homozygous for ΔF508, CFTR (ΔF508 homozygous tracheal epithelial cells (18)) cells were transfected with ΔF508-CFTR-GFP. After 42 hrs of transfection cells were induced with bortezomib (10 µM) for 6 hrs. There was a significant increase in the accumulation and stabilization of the B form with 10 µM bortezomib as compared to untreated control, as shown in FIG. 2C. S9 cells transfected with wt-CFTR and exposed to bortezomib similarly produced substantial amounts of mature band C (FIG. 2B).

Figure 2D:
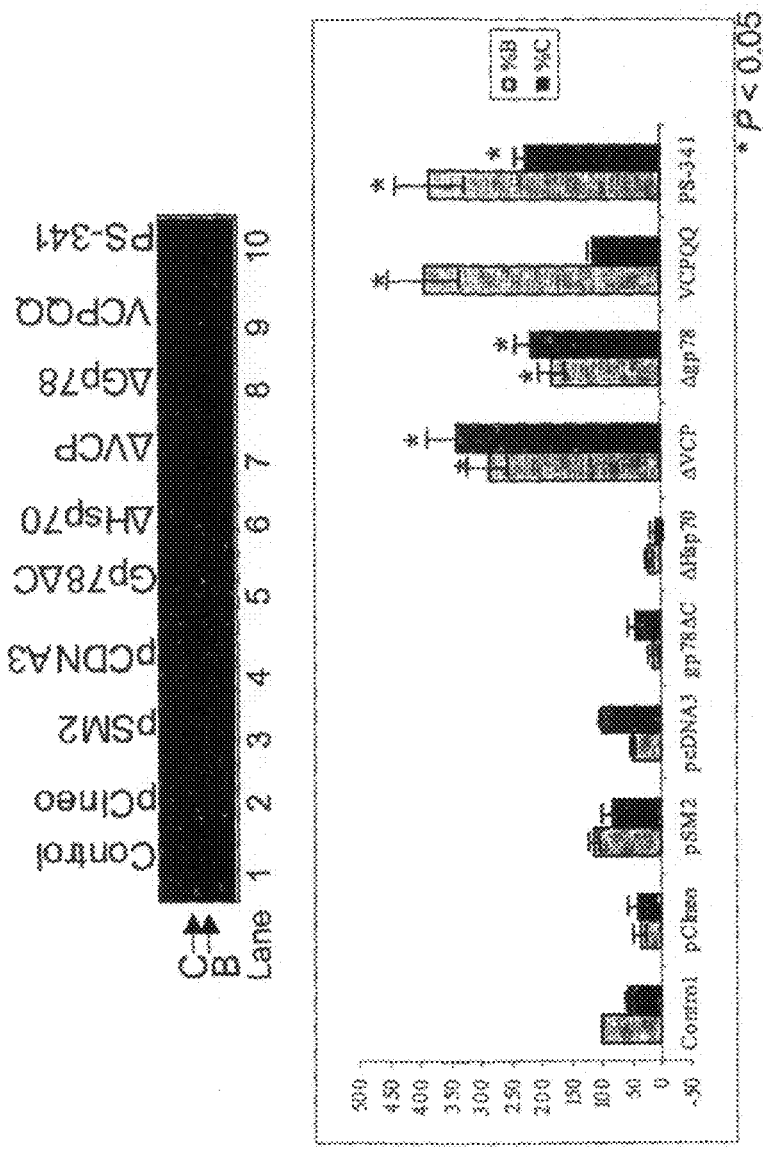

To study the effect of inhibiting components of ubiquitination and proteasomal degradation in endoplasmic reticulum associated degradation (BRAD), the relative basal levels of immature B and mature C form of ΔF508-CFTR in IB3-1 cells were compared by metabolic labeling (t=2 hrs) (lane 1, FIG. 2D). There were no observed changes in levels of B and C forms of ΔF508-CFTR on transfecting IB3-1 cells with empty vectors (pCIneo/pcDNA3/pSM2) as compared to control (lanes 2-4, FIG. 2D). In contrast both VCP and gp78 inhibition resulted in accumulation of B form as compared to control, while C form showed a more significant increase with VCP inhibition as compared to a minimal increase with gp78 inhibition (lanes 7 and 8, FIG. 2D). Since VCP physically interacts with gp78(8) it is expected that the gp78-VCP interaction may represent one way of coupling ubiquitination with retro-translocation and degradation of ΔF508-CFTR. To evaluate the effect of this interaction on endoplasmic reticulum associated degradation (ERAD) of ΔF508-CFTR, a gp78ΔC construct deficient in the VCP binding domain was used. No change in levels of B and C forms of ΔF508-CFTR as compared to control were observed (lane 5, FIG. 2D), thus suggesting that this gp78-VCP interaction is required for endoplasmic reticulum associated degradation (ERAD) of ΔF508-CFTR. Moreover the VCPQQ construct, which is deficient in two AAA ATPase domains, D1 & D2, partially rescued the B and C form of ΔF508-CFTR (lane 9, FIG. 2D), indicating that two AAA ATPase domains are involved in endoplasmic reticulum associated degradation (ERAD) of ΔF508-CFTR. The levels of B and C form were lower after transfection with VCP QQ construct as compared to complete VCP gene inhibition (ΔVCP), probably due to residual VCP AAA ATPase domain activity. Interference with HSP70 expression (lane 6, FIG. 2D) did not rescue CFTR, which is expected because it is the increase in expression of HSP70 that promotes the maturation of band B to C (19). The inhibition of proteasomal mediated degradation by bortezomib partially rescued ΔF508-CFTR from endoplasmic reticulum associated degradation (ERAD) (lane, 10, FIG. 2D). To investigate the effects of bortezomib on components of endoplasmic reticulum associated degradation (ERAD), IB3-1 cells were treated with bortezomib for 6 hr and then immunoblotted for ERAD components. Induction of Hsp70 and inhibition of VCP were observed with no change in gp78 and Hsp40, as shown in FIG. 3A.

In summary, these data show that VCP/p97 inhibition rescues ΔF508-cystic fibrosis transmembrane receptor from endoplasmic reticulum associated degradation.

Example 3

VCP/p97 Interacts with Cystic Fibrosis Transmembrane Receptor Immune-Complex

To confirm that both ΔF508 and wt-cystic fibrosis transmembrane receptor (CFTR) are VCP substrates, CFTR was immunoprecipitated from IB3-1 and S9 total protein extracts (500 µg/ml), respectively using rabbit anti-CFTR 169 polyclonal antibody (15). IB3-1 cells were transfected with ΔF508-CFTR for 48 hrs, metabolically labeled for 30 min with TRAN-35S-label, and chased for the indicated time points. The graphs on the bottom represent a quantitation of the results shown on the top. The ΔF508-CFTR was immunoprecipitated using rabbit polyclonal anti-CFTR 169 antibody. FIG. 3A shows IB3-1 cells transfected with ΔF508-CFTR and co-transfected with ΔVCP or Δgp78 for 48 hrs. VCP/gp78 inhibition results in accumulation of ΔF508-CFTR (B-form) and partial rescue of mature (C-form). (VCP was co-immunoprecipitated with both ΔF508 and wt-CFTR (FIG. 3B, left panel), indicating VCP to be the integral component of endoplasmic reticulum associated degradation (ERAD) of CFTR. It is possible that VCP may be interacting with residual ΔF508-CFTR in the S9 cell line. VCP antibody was used as a positive control, while a pre-immune serum was used as a negative control for immunoprecipitation from IB3-1 cells. VCP also was found to co-immunoprecipitate with Hsp40, probably as a part of the ΔF508-CFTR immunocomplex from IB3-1 cells (FIG. 3C).

To understand the mechanism of VCP mediated endoplasmic reticulum associated degradation of CFTR, the interaction of VCP with other molecular chaperones known to be associated with ΔF508- or wt-CFTR degradation machinery was examined. CFTR, Hsp40, Hsp90, Hsc70, Hsp70, CHIP and VCP were immunoprecipitated from IB3-1 and S9 total protein extracts (500 µg/ml) to evaluate relative VCP levels from each IB3-1 and S9 immunoprecipitate. VCP was independently co-immunoprecipitated with ΔF508-CFTR, Hsp40, Hsp90, Hsc70, Hsp70 and CHIP from IB3-1 cells, as shown in FIG. 4A). Relatively higher amounts of VCP were pulled down with Hsp40 and Hsc70 antisera as compared to other proteins, suggesting a stronger interaction or a higher stoichiometry. VCP was pulled down together with Hsp90 and Hsp70 immunocomplexes from IB3-1 cells but not S9, as shown in FIG. 4A. Moreover, VCP had higher stoichiometry for these molecular chaperones in presence of ΔF508 CFTR (IB3-1) as compared to wt-CFTR (S9). Freshly isolated bronchial epithelial cells brushed from cystic fibrosis patients homozygous for ΔF508 CFTR, were examined by immunoprecipitation of individual components of ERAD, followed by immunoblotting for VCP or Hsc70 (FIG. 4B). Again, VCP and Hsc70 were prominent with anti-Hsp40. These data show that VCP/p97 interacts with cystic fibrosis transmembrane receptor immune-complex.

Example 4

VCP Inhibition and Bortezomib Treatment Induce Chloride Efflux

Figure 5C:
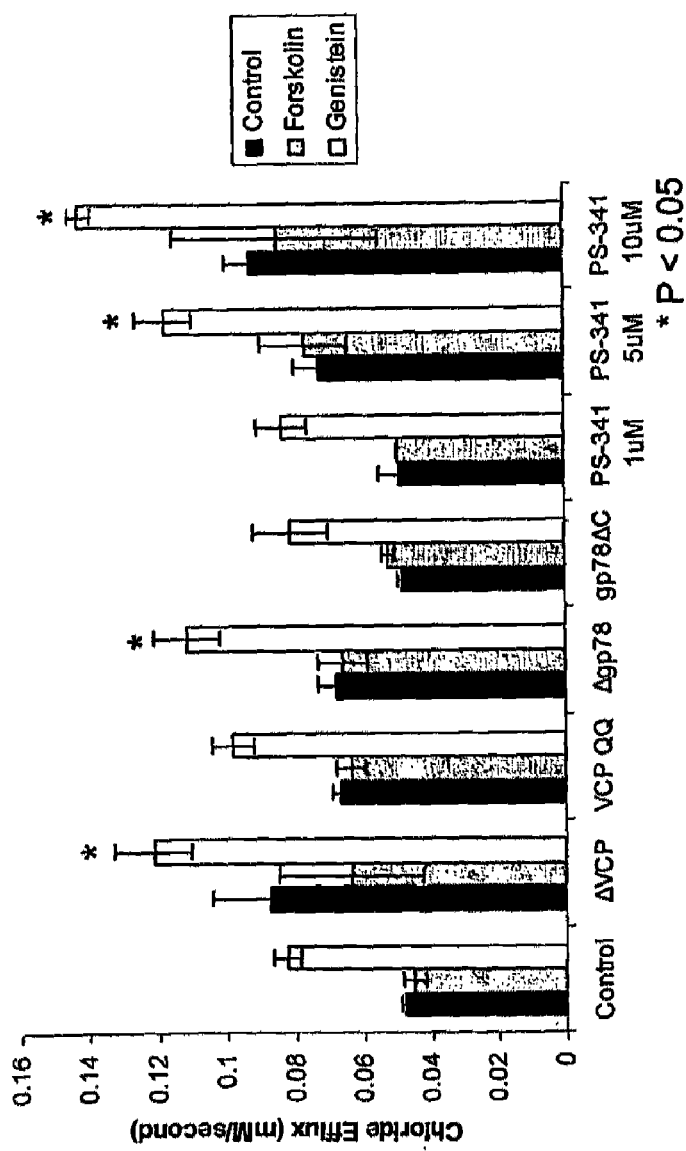
FIG. 5 (A-C) are three graphs that show induction of cAMP mediated cystic fibrosis transmembrane receptor chloride efflux in IB3-1 cells by VCP/gp78 and proteasome inhibition. (A) IB3-1 cells were treated with forskolin or genistein. At t=4 minutes (min) no cAMP cells were treated with 172 (a cystic fibrosis transmembrane receptor) inhibitor or 14-22 amide (cAMP inhibitor). Genistein treatment show a significant increase in MQAE fluorescence, but forskolin treatment showed no significant change from no cAMP control. Both 172 inhibitor treatment and 14-22 amide-treatment block the cAMP mediated cystic fibrosis transmembrane receptor (CFTR) activity. Each bar represents n=3±SD. Both CFTR (172) and cAMP (14-22 amide) inhibitors suppress MQAE fluorescence, indicating presence of endogenous cAMP in IB3-1 cells. (B) IB3-1 cells were transfected with ΔF508-CFTR and co-transfected with VCPshRNA or gp78siRNA. Genistein was added at t=0 min and MQAE fluorescence was recorded every min from t=0 to 7 min. Both VCP and gp78 inhibition led to a significant increase in MQAE fluorescence indicative of Cl-activity. VCP inhibition rescues functional ΔF508-CFTR by t=5 min. Data are the mean±SD of three experiments. (C) IB3-1 cells were transfected with ΔF508-CFTR and co-transfected with ΔVCP, VCPQQ, Δgp78, gp78ΔC or treated with bortezomib (0, 5 or 10 µM) for 6 hrs. Macroscopic halide permeability was monitored for transfected or bortezomib treated IB3-1 cells by using fluorescence based (MQAE) assay. Each bar represents the mean change in chloride efflux (mM/s)±SD in fixed microscopic area from three different experiments. ΔVCP, VCPQQ, Δgp78 and bortezomib (5 or 10 µM) significantly induced genistein mediated chloride efflux.

To confirm that ΔF508-CFTR rescue from endoplasmic reticulum associated degradation led to functional cell surface chloride channels, cAMP-stimulated halide efflux in IB3-1 cells was measured (FIGS. 5A and B). The IB3-1 cells were transfected with ΔF508-CFTR-GFP, and co-transfected with ΔVCP, VCPQQ, Δgp78, gp78ΔC, or treated with bortezomib (1, 5 or 10 µM) for 6 hrs. There was minimal or no change in MQAE fluorescence, which is indicative of Cl⁻ channel activity, when the cells were stimulated by forskolin, although there was a significant change in fluorescence as a result of genistein treatment, as shown in FIG. 5A. Genistein is an isoflavonoid that directly activates CFTR chloride channels (20). Acute exposure to genistein augmented chloride efflux in ΔVCP, Δgp78 and 5 or 10 µM bortezomib treatments, thus suggesting a surface localization for ΔF508-CFTR (FIG. 5C). These results indicate that inhibiting VCP/gp78 or proteasome activity by bortezomib can rescue functional ΔF508-CFTR to the cell surface, resulting in a functional increase in cell surface chloride transport detectable with agonist. Moreover, bortezomib/ΔVCP and genistein have a synergistic effect on the rescue of functional ΔF508-CFTR from endoplasmic reticulum associated degradation (ERAD) (FIG. 5C), probably by improving both CFTR trafficking and function. Together these data demonstrate the expression of functional ΔF508-CFTR in IB3-1 cells by either bortezomib treatment or selective inhibition of VCP.

Example 5

Figure 6A:
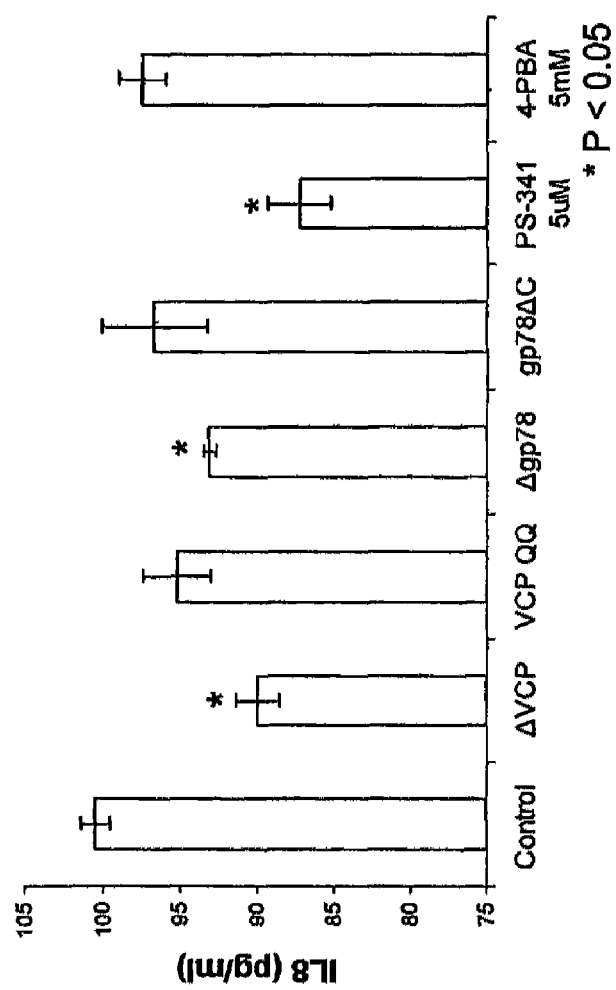
FIG. 6 (A-C) are three graphs that show that VCP inhibition and bortezomib treatment downregulate IL8 cytokine levels. (A) IB3-1 cells were transfected (48 hrs) with ΔVCP, VCPQQ, Δgp78, gp78ΔC or treated with 5 µM bortezomib (6 hrs)/5 mM 4PBA (48 hrs). Cells were induced with IL1-β (1 ng/ml) for 12 hrs. The percent average IL8 cytokine levels (n=3)±SD of three independent experiments is shown. IL8 cytokine levels are significantly inhibited by ΔVCP, Δgp78 and bortezomib as compared to control or VCPQQ, gp78ΔC and 4-PBA. (B) IB3-1 cells were transfected (24 hrs) with ΔVCP, ΔF508, ΔCHOP or treated with 5 µM bortezomib (6 hrs)/5 µM MLN-273 (6 hrs)/5 mM 4PBA (24 hrs). Cells were induced with IL1-β (1 ng/ml) for 12 hrs. The percent average IL8 cytokine levels (n=3)±SD of three independent experiments is shown. IL8 cytokine levels are significantly inhibited by ΔVCP, MLN273 and bortezomib as compared to control or ΔCHOP and 4-PBA. ΔCHOP and bortezomib have synergistic effect on IL8 down regulation. (C) IB3-1 cells were transfected (24 hrs) with ΔVCP, ΔF508, ΔCHOP or treated with 5 µM bortezomib (6 hrs)/5 µM MLN-273 (6 hrs)/5 mM 4PBA (24 hrs). Cells were induced with IL1-β (1 ng/ml) for 12 hrs. The absorbance at 450 nm is directly proportional to bound NFκB. The binding of NRB was significantly inhibited by ΔVCP, MLN273 and bortezomib as compared to control or ΔCHOP and 4-PBA. ΔCHOP and bortezomib have synergistic effect on NFκB binding. Each bar represents absorbance at 450 nm (n=3)±SD.

VCP Inhibition and Bortezomib Treatment Downregulate IL8 Cytokine Levels and NFκB Binding It has been shown that human bronchial epithelial cells expressing ΔF508-CFTR generate more IL8 in response to TNFα, IL1-β or *P. aeruginosa*(21,22). After cell stimulation, IκB-α is phosphorylated and degraded by the 26S proteasome resulting in nuclear transport of NFκB followed by IL8 gene activation (23). To evaluate the effect of VCP mediated ERAD on the NFκB mediated inflammatory response, IL8 cytokine levels were quantified in IB3-1 cells. The IB3-1 cells were transfected with ΔVCP, VCPQQ, Δgp78 and gp780C constructs, and treated with 5 μM bortezomib or 5 mM 4-Phenylbutyrate (4PBA), a histone deacetylase inhibitor that induces Hsp70(19). The ΔVCP, Δgp78 and bortezomib significantly downregulated IL8 levels as compared to control or VCPQQ, gp78ΔC and 4-PBA, as shown in FIG. 6A.

Figure 6B:
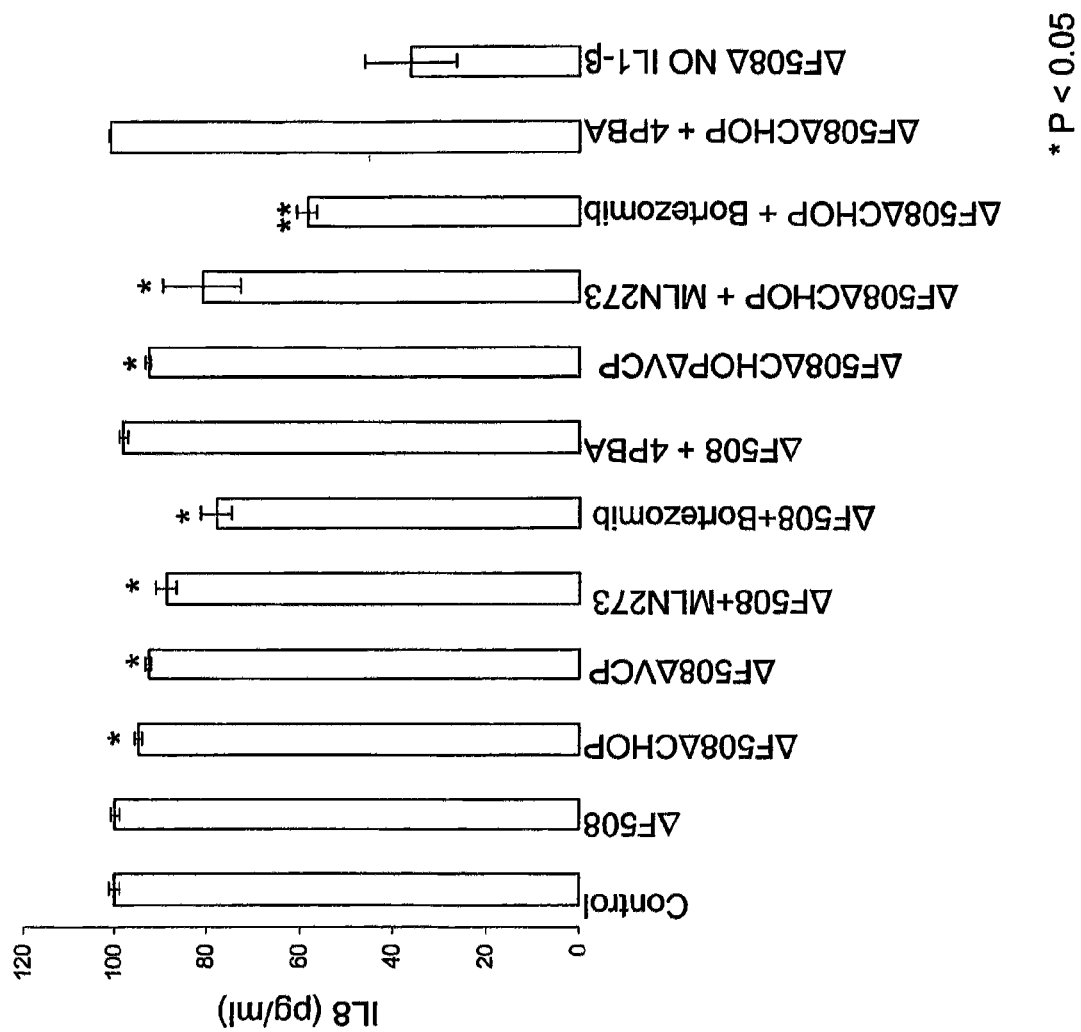
Figure 6C:
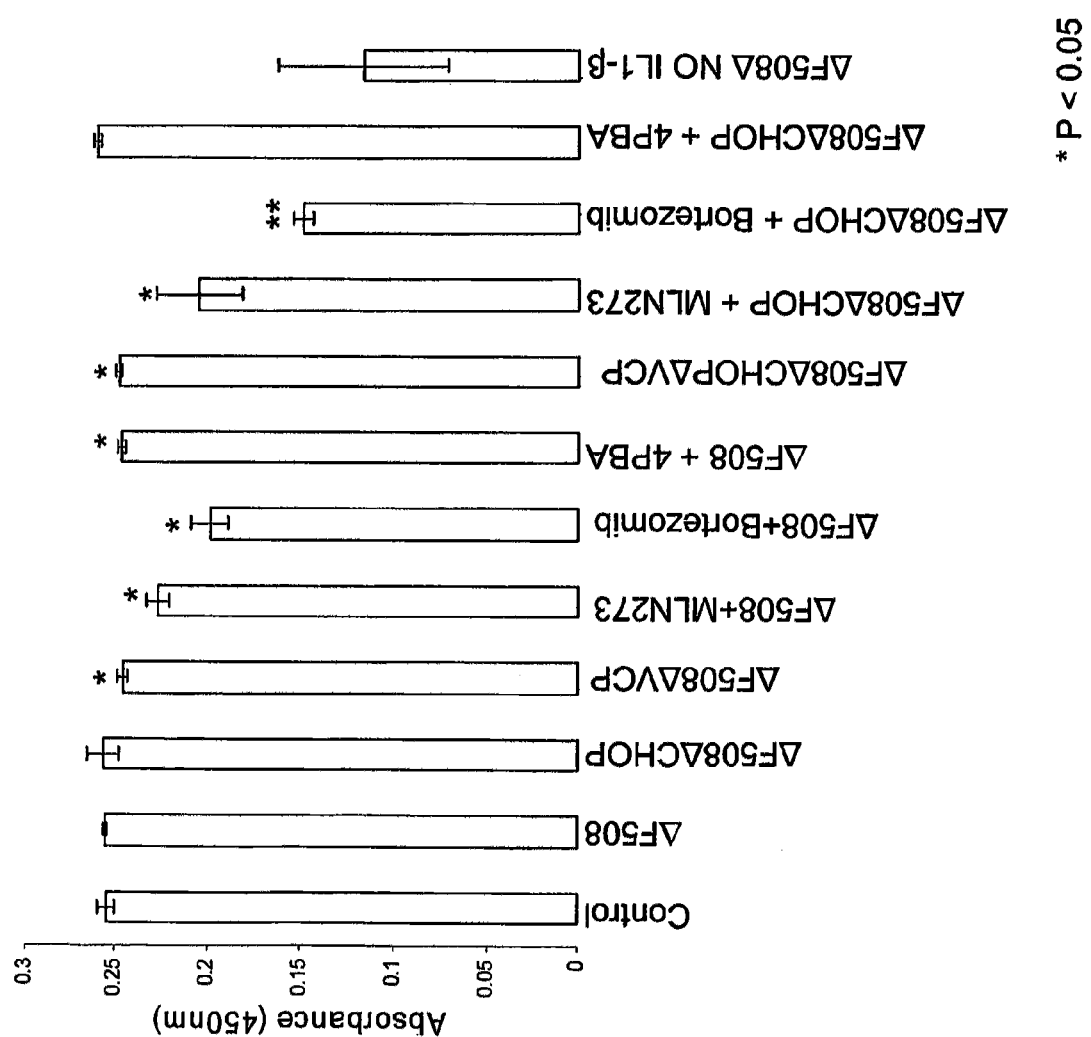

To confirm that down regulation of IL8 levels were NFκB-mediated, NFκB-binding and IL8 levels in IB3-1 cells was evaluated. IB3-1 cells were transfected (24 hrs) with ΔVCP, ΔF508, ΔCHOP, or treated with 5 μM bortezomib (6 hrs)/5 μM MLN-273 (6 hrs), a novel small molecule proteasome inhibitor/5 mM 4PBA (24 hrs). CHOP shRNA mediated CHOP inhibition (ΔCHOP) was used to suppress the oxidative stress in response to VCP or proteasome inhibition. Cells were induced with IL1-β (1 ng/ml) for hrs. The supernatants and nuclear extracts from the same experiment were used to determine IL8 levels and NFκB binding. NFκB binding and IL8 cytokine levels were significantly inhibited by ΔVCP, MLN273 and bortezomib, as compared to control or ΔCHOP and 4-PBA. ΔCHOP and bortezomib had a synergistic effect on NFκB binding and IL8 down regulation, as shown in FIGS. 6B & C. The IL8 inhibition by VCP interference is can be explained by IκBα mediated NFκB inhibition. Further, it is known that bortezomib can enter mammalian cells and inhibit NF-κB activation and NF-κB-dependent gene expression. Bortezomib also inhibits TNF-α-induced gene expression of the cell-surface adhesion molecules E-selectin, ICAM-1, and VCAM-1 on primary human umbilical vein endothelial cells (44,45). In a rat model of streptococcal cell wall-induced polyarthritis (46), bortezomib attenuated the neutrophil-predominant acute phase and markedly inhibited the progression of the T cell-dependent chronic phase of the inflammatory response (44).

Together, these results indicate that VCP or proteasome inhibition appear to be the most promising therapeutic strategies to simultaneously restore CFTR trafficking and to inhibit the IκBα degradation (16,17), and hence NFκB-mediated, IL8 activation.

Two representative mammalian U-box proteins, Ufd2 and CHIP, interact with the molecular chaperones VCP and either Hsp90 or Hsc70, respectively and are implicated in the degradation of damaged proteins (31). The combination of CHIP with Hsp90 mediates ubiquitylation of the glucocorticoid receptor, and CHIP together with Hsc70 is known to target immature CFTR for proteasomal degradation (32,33). The data herein shows that VCP is directly associated with CFTR and requisite for ERAD of CFTR, but it is not clear if both VCP and CHIP mediated pathways operate parallel to each other. Certainly VCP is also involved in retro-translocation of tagged protein from ER to proteasome indicating that it may be involved in steps after CHIP.

Figure 7:
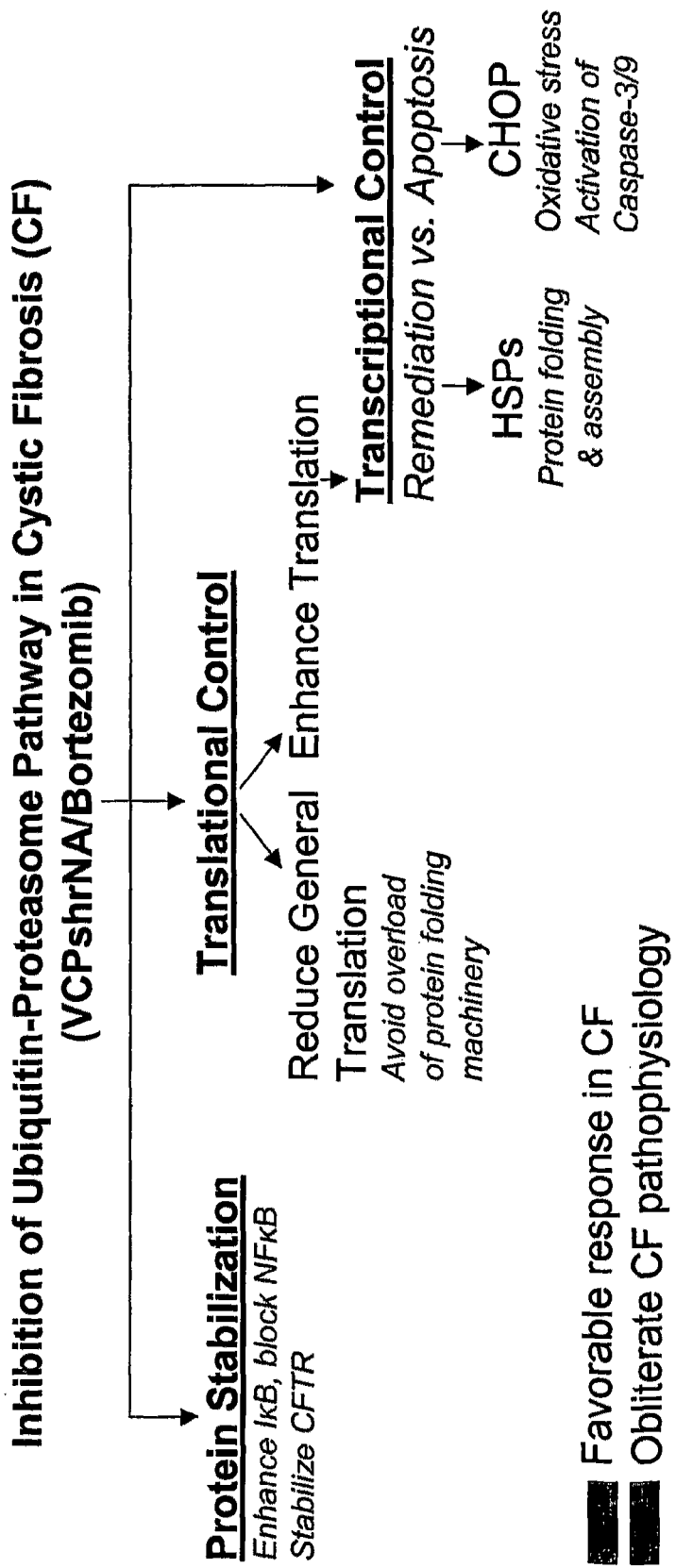
FIG. 7 is a schematic diagram illustrating the inhibition of ubiquitin-proteasome pathway in cystic fibrosis (CF). Proteasome or VCP inhibition stabilizes IκB and blocks NRB mediated interleukin 8 (IL8) activation in addition to rescuing CFTR from degradation. The inhibition of ubiquitin-proteasome pathway reduces general translation to avoid overload of protein folding machinery, and enhance translation and transcription of specific transcription factors like heat shock proteins (HSPs) to enhance protein folding and assembly and C/EBP homologous protein (CHOP) to induce oxidative stress and apoptosis.

Taken together, the data presented herein show that VCP is the integral component of ERAD and ER stress pathways induced by UPR in CF, and may be central to the efficacy of CF drugs that target the ubiquitin proteasome system. Modulating proteasomal degradation by bortezomib or VCP shRNA rescues the functional mutant CFTR to the cell surface and suppresses NFκB mediated IL8 activation. FIG. 7 is a schematic illustrating that proteasome or VCP inhibition stabilizes IκB and blocks NFκB mediated interleukin 8 (IL8) activation in addition to rescuing CFTR from degradation. The inhibition of ubiquitin-proteasome pathway reduces general translation to avoid overload of protein folding machinery, and enhance translation and transcription of specific transcription factors like heat shock proteins (HSPs) to enhance protein folding and assembly and C/EBP homologous protein (CHOP) to induce oxidative stress and apoptosis.

This ability to ameliorate secondary aspects of CF disease pathophysiology in addition to rescue of CFTR to the cell surface is promising for CF therapeutics. Moreover, identification and selective modulation of ERAD components as potential therapeutics for a wide range of human diseases associated with ERAD promises fertile area of investigation.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof. All patents and publications mentioned in this specification are herein incorporated by reference to the same extent as if each independent patent and publication was specifically and individually indicated to be incorporated by reference.

REFERENCES

1. Rock, K. L., and Goldberg, A. L. (1999) Annu Rev Immunol 17, 739-779
2. Meusser, B., Hirsch, C., Jarosch, E., and Sommer, T. (2005) Nat Cell Biol 7(8), 766-772
3. Ward, C. L., Omura, S., and Kopito, R. R. (1995) Cell 83(1), 121-127
4. Rowe, S. M., Miller, S., and Sorscher, E. J. (2005) N Engl J Med 352(19), 1992-2001
5. Denning, G. M., Anderson, M. P., Amara, J. F., Marshall, J., Smith, A. E., and Welsh, M. J. (1992) Nature 358(6389), 761-764
6. Wang, Q., Song, C., and Li, C. C. (2004) J Struct Biol 146(1-2), 44-57
7. Ye, Y., Meyer, H. H., and Rapoport, T. A. (2003) J Cell Biol 162(1), 71-84

8. Zhong, X., Shen, Y., Balla; P., Apostolou, A., Agami, R., and Fang, S. (2004) J Biol Chem 279(44), 45676-45684
9. Gnann, A., Riordan, J. R., and Wolf, D. H. (2004) Mol Biol Cell 15(9), 4125-4135
10. Lim, M., McKenzie, K., Floyd, A. D., Kwon, E., and Zeitlin, P. L. (2004) Am J Respir Cell Mol Biol 31(3), 351-357
11. Dignam, J. D., Lebovitz, R. M., and Roeder, R. G. (1983) Nucleic Acids Res 11(5), 1475-1489
12. Ma, T., Thiagarajah, J. R., Yang, H., Sonawane, N. D., Folli, C., Galietta, L. J., and Verkman, A. S. (2002) J Clin Invest 110(11), 1651-1658
13. Zeitlin, P. L., Lu, L., Rhim, J., Cutting, G., Stetten, G., Kieffer, K. A., Craig, R., and Guggino, W. B. (1991) Am J Respir Cell Mol Biol 4(4), 313-319
14. Sharma, M., Benharouga, M., Hu, W., and Lukacs, G. L. (2001) J Biol Chem 276(12), 8942-8950
15. Crawford, I., Maloney, P. C., Zeitlin, P. L., Guggino, W. B., Hyde, S. C., Turley, H., Gaffer, K. C., Harris, A., and Higgins, C. F. (1991) Proc Natl Acad Sci USA 88(20), 9262-9266
16. Dai, R. M., Chen, E., Longo, D. L., Gorbea, C. M., and Li, C. C. (1998) J Biol Chem 273(6), 3562-3573
17. Hideshima, T., Chauhan, D., Richardson, P., Mitsiades, C., Mitsiades, N., Hayashi, T., Munshi, N., Dang, L., Castro, A., Palombella, V., Adams, J., and Anderson, K. C. (2002) J Biol Chem 277(19), 16639-16647
18. Kunzelmann, K., Schwiebert, E. M., Zeitlin, P. L., Kuo, W. L., Stanton, B. A., and Gruenert, D. C. (1993) Am J Respir Cell Mol Biol 8(5), 522-529
19. Choo-Kang, L. R., and Zeitlin, P. L. (2001) Am J Physiol Lung Cell Mol Physiol 281(1), L58-68
20. Moran, O., and Zegarra-Moran, O. (2005) FEBS Lett 579(18), 3979-3983
21. DiMango, E., Zar, H. J., Bryan, R., and Prince, A. (1995) J Clin Invest 96(5), 2204-2210
22. Srivastava, M., Eidelman, O., Zhang, J., Paweletz, C., Caohuy, H., Yang, Q., Jacobson, K. A., Heldman, E., Huang, W., Jozwik, C., Pollard, B. S., and Pollard, H. B. (2004) Proc Natl Acad Sci USA 101(20), 7693-7698
23. Siebenlist, U., Franzoso, G., and Brown, K. (1994) Annu Rev Cell Biol 10, 405-455
24. Yen, C. H., Yang, Y. C., Ruscetti, S. K., Kirken, R. A., Dai, R. M., and Li, C. C. (2000) J Immunol 165(11), 6372-6380
25. Dai, R. M., and Li, C. C. (2001) Nat Cell Biol 3(8), 740-744
26. Kaneko, C., Hatakeyama, S., Matsumoto, M., Yada, M., Nakayama, K., and Nakayama, K. I. (2003) Biochem Biophys Res Commun 300(2), 297-304
27. Matsumoto, M., Yada, M., Hatakeyama, S., Ishimoto, H., Tanimura, T., Tsuji, S., Kakizuka, A., Kitagawa, M., and Nakayama, K. I. (2004) Embo J 23(3), 659-669
28. Ye, Y., Meyer, H. H., and Rapoport, T. A. (2001) Nature 414(6864), 652-656
29. Bays, N. W., Wilhovsky, S. K., Goradia, A., Hodgkiss-Harlow, K., and Hampton, R. Y. (2001) Mol Biol Cell 12(12), 4114-4128
30. Dalal, S., Rosser, M. F., Cyr, D. M., and Hanson, P. I. (2004) Mol Biol Cell 15(2), 637-648
31. Hatakeyama, S., Matsumoto, M., Yada, M., and Nakayama, K. L (2004) Genes Cells 9(6), 533-548
32. Connell, P., Ballinger, C. A., Jiang, J., Wu, Y., Thompson, L. J., Hohfeld, J., and Patterson, C. (2001) Nat Cell Biol 3(1), 93-96
33. Meacham, G. C., Patterson, C., Zhang, W., Younger, J. M., and Cyr, D. M. (2001) Nat Cell Biol 3(1), 100-105
34. Johnston, J. A., Ward, C. L., and Kopito, R. R. (1998) J Cell Biol 143(7), 1883-1898
35. Younger, J. M., Ren, H. Y., Chen, L., Fan, C. Y., Fields, A., Patterson, C., and Cyr, D. M. (2004) J Cell Biol 167(6), 1075-1085
36. Oberdorf, J., Carlson, E. J., and Skach, W. R. (2006) J Cell Sci
37. Mitchell, B. S. (2003) N Engl J Med 348(26), 2597-2598
38. Bross, P. F., Kane, R., Farrell, A. T., Abraham, S., Benson, K., Brower, M. E., Bradley, S., Gobburu, J. V., Goheer, A., Lee, S. L., Leighton, J., Liang, C. Y., Lostritto, R. T., McGuinn, W. D., Morse, D. E., Rahman, A., Rosario, L. A., Verbois, S. L., Williams, G., Wang, Y. C., and Pazdur, R. (2004) Clin Cancer Res 10(12 Pt 1), 3954-3964
39. Kane, R. C., Bross, P. F., Farrell, A. T., and Pazdur, R. (2003) Oncologist 8(6), 508-513
40. Adams, J. (2001) Semin Oncol 28(6), 613-619
41. Zhang, L. N., Karp, P., Gerard, C. J., Pastor, E., Laux, D., Munson, K., Yan, Z., Liu, X., Godwin, S., Thomas, C. P., Zabner, J., Shi, H., Caldwell, C. W., Peluso, R., Carter, B., and Engelhardt, J. F. (2004) Mol Ther 10(6), 990-1002
42. Khan, T. Z., Wagener, J. S., Bost, T., Martinez, J., Accurso, F. J., and Riches, D. W. (1995) Am J Respir Crit. Care Med 151(4), 1075-1082
43. Konstan, M. W., Hilliard, K. A., Norvell, T. M., and Berger, M. (1994) Am J Respir Crit. Care Med 150(2), 448-454
44. Palombella, V. J., Conner, E. M., Fuseler, J. W., Destree, A., Davis, J. M., Laroux, F. S., Wolf, R. E., Huang, J., Brand, S., Elliott, P. J., Lazarus, D., McCormack, T., Parent, L., Stein, R., Adams, J, and Grisham, M. B. (1998) Proc Natl Acad Sci USA 95(26), 15671-15676
45. Read, M. A., Neish, A. S., Luscinskas, F. W., Palombella, V. J., Maniatis, T., and Collins, T. (1995) Immunity 2(5), 493-506
46. Cromartie, W. J., Craddock, J. G., Schwab, J. H., Anderle, S. K., and Yang, C. H. (1977) J Exp Med 146(6), 1585-1602
47. Rao, R. V., Poksay, K. S., Castro-Obregon, S., Schilling, B., Row, R. H., del Rio, G., Gibson, B. W., Ellerby, H. M., and Bredesen, D. E. (2004) J Biol Chem 279(1), 177-187
48. Kitiphongspattana, K., Mathews, C. E., Leiter, E. H., and Gaskins, H. R. (2005) J Biol Chem 280(16), 15727-15734 Jiang, H. Y., and Wek, R. C. (2005) J Biol Chem 280(14), 14189-14202
50. Bobadilla, J. L., Macek, M. Jr., Fine, J. P., and Farrell, P. M. 2002. Cystic fibrosis: a worldwide analysis of CFTR mutations—correlation with incidence data and application to screening [review]. Hum. Mutat. 19::575-606.
51. Pilewski, J. M., and Frizzell, R. A. Role of CFTR in airway disease. 1999. Physiol. Rev. 79::S215-S255
52. Sheppard, D. N., and Welsh, M. J. 1999. Structure and function of the CFTR chloride channel. *Physiol. Rev.* 79:: S23-S45.
53. Denning, G. M. et al. 1992. Processing of mutant cystic fibrosis transmembrane conductance regulator is temperature-sensitive. Nature. 358:761-764.
54. Lukacs, G. L. et al. 1994. Conformational maturation of CFTR but not its mutant counterpart (F508) occurs in the endoplasmic reticulum and requires ATP. EMBO J. 13:: 6076-6086.
55. Sharma, M., Benharouga, M., Hu, W., and Lukacs, G. L. 2001. Conformational and temperature-sensitive stability defects of the F508 cystic fibrosis transmembrane conductance regulator in post-endoplasmic reticulum compartments. J. Biol. Chem. 276::8942-8950.
56. Vij N, Fang S, Zeitlin P L. 2006. Selective inhibition of ERAD rescues ΔF508-CFTR and suppresses IL8 levels: therapeutic implications. J Biol. Chem. 23; 281(25):17369-78.

What is claimed is:

1. A method of treating cystic fibrosis in an individual in need of such treatment, comprising the step of administering one or more inhibitors each of which is capable of reducing cellular degradation of cystic fibrosis transmembrane regulator, wherein the one or more inhibitors are selected from the group consisting of a p97/valosin-containing protein inhibitor, a gp78 inhibitor, and a proteasome inhibitor.

* * * * *